United States Patent
Bhatia et al.

(10) Patent No.: US 6,221,663 B1
(45) Date of Patent: Apr. 24, 2001

(54) CO-CULTIVATION OF CELLS IN A MICROPATTERNED CONFIGURATION

(75) Inventors: Sangeeta Bhatia, Cambridge; Martin Yarmush, Newton; Mehmet Toner, Wellesley, all of MA (US)

(73) Assignee: The General Hospital Corporation Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/482,017

(22) Filed: Jan. 13, 2000

Related U.S. Application Data

(62) Division of application No. 08/943,143, filed on Oct. 3, 1997, now Pat. No. 6,133,030.
(60) Provisional application No. 60/046,413, filed on May 14, 1997.

(51) Int. Cl.[7] .............. C12N 5/00; C12N 11/02

(52) U.S. Cl. ............ 435/373; 435/395; 435/402; 435/289.1; 435/305.1; 435/309.1; 435/177

(58) Field of Search .................. 435/373, 375, 435/395, 370–372, 402, 392, 177, 70.1, 70.3, 69.1

(56) References Cited

U.S. PATENT DOCUMENTS

| | | | |
|---|---|---|---|
| 4,559,304 | 12/1985 | Kasai et al. | 435/392 |
| 4,614,517 | 9/1986 | Ruoslahti et al. | 623/11 |
| 5,108,926 | 4/1992 | Klebe | 435/286.4 |
| 5,202,227 | 4/1993 | Matsuda et al. | 430/320 |
| 5,470,739 | 11/1995 | Akaike et al. | 435/402 |
| 5,573,942 | 11/1996 | Miyamoto | 435/402 |
| 5,602,029 | 2/1997 | Miyamoto | 435/395 |

OTHER PUBLICATIONS

Clark et al.; Exp. Cell. Res. vol. 230; pp. 275–283.
Ireland; "Effect of patterned surfaces of adhesive islands on the shape, cytoskeleton, adhesion and behaviour of swiss mouse 3T3 Fibroblasts"; J. Cell. Sci. Suppl. 8:19–33; (1987).
Berthiaume et al.; "Effect of extracellular matrix topology on cell structure, function, and physiological responsiveness: hepatocytes cultured in a sandwich configuration"; FASEB J 10:1471–1484 (1996).
Bhatia et al.; "Development of a potential bioartificial liver: selective adhesion of hepatocytes"; Master of Science Thesis; Massachusetts Institute of Technology (1993).
Bhatia et al. "Selective adhesion of hepatocytes on patterned surfaces"; Annals of the New York—cademy of Sciences 745:187–209 (1991).
Bhatia et al.; "Controlling cell interactions by micropatterning in co–cultures: hepatocytes and 3T3 fibroblasts"; Journal of Biomedical Materials Research 34(2):189–199 (1997).
Corey et al.; "Compliance of hippocampal neurons to patterned substrate networks"; Journal of Neuroscience Research 30:300–307; (1991).
Britland et al.; "Micropatterning proteins and synthetic peptides on solid supports: a novel application for microelectronics fabrication technology"; Biotechnology Progress 8:155–160; (1992).
Dunn et al.; "Long–term in vitro function of adult hepatocytes in a collagen sandwich configuration"; Biotechnology Progress 7:237–245 (1991).
Dunn et al.; "Hepatocytes in collagen sandwich: evidence for transcriptional and translational regulation"; Journal of Cell Biology 116(4):1043–1053 (1992).

(List continued on next page.)

Primary Examiner—Christopher R. Tate
(74) Attorney, Agent, or Firm—Fish & Richardson P.C.

(57) ABSTRACT

Disclosed are methods for producing co-cultures of cells in which at least two cell types are present in a micropattern configuration.

22 Claims, 4 Drawing Sheets

OTHER PUBLICATIONS

Dunn et al.; "Long–term culture of differentiated hepatocytes in a collagen sandwich configuration" Doctoral Dissertion; Massachusetts Institute of Technology (1992).

Fillinger et al.; "The effect of endothelial cell coculture on smooth muscle cell proliferation"; Journal of Vascular Surgery 17:1058–1068 (1993).

Clark et al.; "Cell guidance by micropatterned adhesiveness in vitro"; Journal of Cell Science 103:287–292 (1992).

Clark et al.; "Growth cone guidance and neuron morphology on micropatterned laminin surfaces"; Journal of Cell Science 105:203–212 (1993).

Dunn et al.; "Hepatocyte function and extracellular matrix geometry: Long–term culture in a sandwich configuration" FASEB J. 3:174–177 (1989).

Guguen–Guillouzo et al.; "Maintenance and reversibility of active albumin secretion by adult rat hepatocytes co–cultured with another liver epithelial cell type"; Experimental Cell Research 143:47–54 (1983).

John Libbery Eurotext, INSERM:259–284 (1996).

Klebe; Cytoscribing: A method for micropositioning cells and the construction of two– and three–dimensional synthetic tissues; Experimental Cell Research 179:362–373 (1988).

Lom et al.; "A versatile technique for patterning biomolecules onto glass coverslips", Journal of Biochemistry 94:1029–1035 (1983).

Matsuda et al.; "Development of micropatterning technology for cultured cells"; ASAIO Transactions 36:M559–M562 (1990).

Nakamura et al.; "Density dependent growth control of adult rat hepatocytes in primary culture"; Journal of Biochemistry 94:1029–1035 (1983).

Langer et al.; Tissue Engineering; Science 260:920–924 (1993).

Matsuda et al.; "Two–dimensional cell manipulation technology"; ASAIO Journal 38:M243–M247 (1992).

Moghe et al.; "Culture matrix configuration and composition in the maintenance of hepatocyte polarity and function"; Biomaterials 17:373–385 (1996).

Ranieri et al.; "Spatial control of neuronal cell attachment and differentiation on covalently patterned laminin oligopeptide substrates"; International Journal of Developmental Neuroscience 12(8):725–735 (1994).

Rozga et al.; "Development of a bioartificial liver: properties and function of a hollow–fiber module inoculated with cells" Hepatology 17:258–265 (1993).

Wu et al.; "entrapment of hepatocyte spheroids in a hollow fiber bioreactor as a potential bioartifical liver"; Tissue Engineering 1(1):29–40 (1995).

Bhatia et al.; Abstract; American Institute of Chemical Engineers; Annual Meeting; Miami, FL Nov. 12, 1995.

Bhatia et al.; Abstract; Biomedical Engineering Society, Annual Meeting, University Park, PA Oct. 3, 1996.

Bhatia et al.; J. Biomedical Research 34:189–199; Feb. 1997, made publicly available Jan. 29, 1997.

CO-CULTIVATION OF CELLS IN A MICROPATTERNED CONFIGURATION

CROSS-REFERENCE TO RELATED APPLICATION

This application is a divisional of U.S. Ser. No. 08/943,143, filed Oct. 3, 1997, now U.S. Pat. No. 6,133,030, which claims priority under 35 U.S.C. §119 from U.S. Ser. No. 60/046,413, filed May 14, 1997.

STATEMENT AS TO FEDERALLY SPONSORED RESEARCH

This invention was produced, at least in part, with funds from the United States Government under National Institutes of Health Grant DK5270. Therefore, the United States Government may have certain rights in the invention.

BACKGROUND OF THE INVENTION

The invention relates to methods for co-cultivating cells in micropatterned formations (e.g., for the production of bioartificial organs).

Co-cultures of hepatocytes with another cell type have been recognized to prolong cell survival rates, maintain phenotype, and induce albumin secretion in hepatocytes. Such co-cultures have been limited by the inability to manipulate or control the interaction of the two cell types in the culture. Generally, to prepare conventional co-cultures, cells of one type are seeded onto a substrate and allowed to attach; cells of a second type then are seeded on top of the cells of the first type. In such co-cultures, parameters such as cell number are controllable, but the spatial orientation of cells within the co-culture is not controlled (Clement, B., et al. "Long-Term Co-Culture of Adult Human Hepatocytes with Rat Liver Epithelial Cells: Modulation of Albumin Secretion and Accumulation of Extracellular Material" Hepatology 4(3): 373–380 (1984); Schrode, W., et al. "Induction of Glutamine Synthetase in Periportal Hepatocytes by Cocultivation with a Liver Epithelial Cell Line" Euro. J. Cell Biol. 53: 35–41 (1990); Michalopoulos, G., et al., In Vitro 15(10): 796–806 (1979); Guguen-Guillouzo, C., et al. "Maintenance and Reversibility of Active Albumin Secretion by Adult Rat Hepatocytes Co-Cultured with Another Liver Epithelial Cell Type" Experimental Cell Research 143: 47–54 (1983); Begue, J. et al. "Prolonged Maintenance of Active Cytochrome P-450 in Adult Rat Hepatocytes Co-Cultured with Another Liver Cell Type" Hepatology 4(5): 839–842 (1984); Agius, L. "Metabolic Interactions of Parenchymal Hepatocytes and Dividing Epithelial Cells in Co-culture" Biochem. J. 252: 23–28 (1988); and Reid, L. et al. "Culturing Hepatocytes and Other Differentiated Cells" Hepatology 4(3): 548–559 (1984)).

SUMMARY OF THE INVENTION

The invention provides methods for producing co-cultures of cells in which at least two types of cells are configured in a micropattern on a substrate. By using micropatterning techniques to modulate the extent of heterotypic cell-cell contacts, it is now possible to modulate (e.g., upregulate or downregulate) metabolic and/or synthetic functions of cells.

Accordingly, the invention provides a method for producing a micropatterned co-culture containing at least two cell types; the method entails:

i) providing a protein-coated substrate, wherein a protein coating the substrate defines a micropattern on the substrate;

ii) contacting the protein-coated substrate with cells of a first cell type suspended in a first cell medium under conditions such that cells of the first cell type bind the protein of the protein-coated substrate, thereby producing a micropatterned cell-coated substrate; and iii) contacting the micropatterned cell-coated substrate with cells of a second cell type suspended in a second cell medium under conditions such that cells of the second cell type bind the substrate, thereby producing the micropatterned co-culture, wherein one of the cell media is a selective medium and one of the cell media is an attachment medium.

Typically, in practicing the invention, the cells of the first and second cell types are mammalian cells, although the cells may be from two different species (e.g., pigs, humans, rats, mice, etc). The cells can be primary cells, or they may be derived from an established cell line. In an alternative method, one of the cell types is mammalian, and a second cell type is microbial in origin, e.g., fungi or bacteria such as Streptococcus ssp., *Staphylococcus aureus,* or *Staphylococcus epidermis*. Examples of suitable combinations of cells for producing the co-culture include, without limitation:

a) hepatocytes (e.g., primary hepatocytes) and fibroblasts (e.g., normal or transformed fibroblasts, such as NIH 3T3-J2 cells);

b) hepatocytes and at least one other cell type, particularly liver cells, such as Kupffer cells, Ito cells, endothelial cells, and biliary ductal cells;

c) endothelial cells and smooth muscle cells;

d) tumorigenic parenchymal cells and mesenchymal cells;

e) hematopoietic cells and bone marrow cells (e.g., adipocytes, fibroblasts); and f) skin cells (e.g., keratinocytes) and fibroblasts. Other combinations of cells also are within the invention.

The substrate on which the cells are grown can be any biologically compatible material to which cells can adhere, such as glass, polymers (such as fluoropolymers, fluorinated ethylene propylene, polyvinylidene, polydimethylsiloxane, polystyrene, polycarbonate, and polyvinyl chloride), and silicon substrates (such as fused silica, polysilicon, or single silicon crystals).

To produce a micropattern of the co-cultured cell types, protein (i.e., a peptide of at least two amino acids) is first adhered to the substrate in order to define (i.e., produce) a micropattern. The micropattern produced by the protein serves as a "template" for formation of the cellular micropattern. Typically, a single protein will be adhered to the substrate, although two or more proteins may be used to define the micropattern (for example, one micropatterned protein may be used to attract one cell type, while a second micropatterned protein is used to attract a second cell type). In practicing the invention, a variety of techniques can be used to foster selective cell adhesion of two or more cell types to the substrate. Included, without limitation, are methods such as localized protein adsorption, organosilane surface modification, alkane thiol self-assembled monolayer surface modification, wet and dry etching techniques for creating three-dimensional substrates, radiofrequency modification, and ion-implantation (Lom et al., 1993, J. Neurosci. Methods 50:385–397; Brittland et al., 1992, Biotechnology Progress 8:155–160; Singhvi et al., 1994, Science 264:696–698; Singhvi et al., 1994, Biotechnology and Bioengineering 43:764–771; Ranieri et al., 1994, Intl. J. Devel. Neurosci. 12(8):725–735; Bellamkonda et al., 1994, Biotechnology and Bioengineering 43:543–554; and Valentini et al., 1993, J. Biomaterials Science Polymer Edition 5(1/2):13–36).

Proteins that are suitable for producing a micropattern are those proteins to which one of the cell types of the co-culture specifically binds under the cell culture conditions used to cultivate the co-culture (i.e., conventional cell culture conditions). For example, hepatocytes are known to bind to collagen. Therefore, collagen is well-suited to facilitate binding of hepatocytes in a micropattern. Other suitable proteins include fibronectin, gelatin, collagen type IV, laminin, entactin, and other basement proteins, including glycosaminoglycans such as heparan sulfate. Combinations of such proteins also can be used.

Typically, in practicing the invention, the cells of the first cell type (e.g., hepatocytes) initially are suspended in an "selective" cell culture medium (e.g., serum-free medium and media that lack "attachment factors"), while the cells of the second cell type are suspended in an "attachment" medium [e.g., a cell culture medium that contains serum (typically 1–10% (e.g., 5–10%)), or one or more "attachment factors" (typically at least 1 ng/ml (e.g., 5–100 ng/ml)) such as fibronectins and other extracellular matrix, selecting, RGD peptides, ICAMs, E-cadherins, and antibodies that specifically bind a cell surface protein (for example, an integrin, ICAM, selectin, or E-cadherin)].

In another method of practicing of the invention, the cells of the second type have intrinsic attachment capabilities, thus eliminating a need for the addition of serum or exogenous attachment factors. Some cell types will attach to electrically charged cell culture substrates and will adhere to the substrate via cell surface proteins and by secretion of extracellular matrix molecules. Fibroblasts are an example of one cell type that will attach to cell culture substrates under these conditions. Thus, the invention also includes a method for producing a micropatterned co-culture containing at least two cell types where the method entails:

i) providing a protein coated substrate wherein a protein coating the substrate defines a micropattern on the substrate;

ii) contacting the protein-coated substrate with cells of a first cell type suspended in a first cell medium under conditions such that the cells of the first cell type bind the protein of the protein-coated substrate, thereby producing a micropatterned cell-coated substrate; and iii) contacting the micropatterned cell-coated substrate with cells of a second cell type suspended in a second cell medium under conditions such that the cells of the second cell type bind to the substrate, thereby producing the micropatterned co-culture, wherein the first cell type (e.g., dermal fibroblasts of skin) is in non-attachment medium and the second cell type has natural attachment capabilities to attach it to the substrate. A charged substrate is particularly useful in practicing this variation of the invention.

In yet another variation, the micropatterned co-culture can be produced by i) providing a repellent-coated substrate wherein a repellent coating the substrate defines a micropattern on the substrate;

ii) contacting the repellent-coated substrate with cells of a first cell type suspended in a first cell medium under conditions such that cells of the first cell type bind the substrate, thereby producing a micropatterned cell/repellent-coated substrate; and iii) contacting the micropatterned cell/repellent-coated substrate with cells of a second cell type suspended in a second cell medium under conditions such that cells of the second cell type bind the repellent, thereby producing the micropatterned co-culture.

As used herein, a "repellent" is a composition that, relative to the substrate to which it is applied, inhibits adhesion of the first-applied cells, thereby causing the first-applied cells to adhere preferentially to the substrate. Agarose, hyaluronic acid, and alginate are examples of suitable repellents. In this variation, the cells of the first cell type (e.g., hepatocytes) can be suspended in a selective medium or in a selective medium. If desired, binding of cells of the first cell type to the substrate can be facilitated by using a substrate that is coated with a protein to which the cells of the first type specifically bind, as described above. The cells of the second cell type (e.g., fibroblasts) can be suspended in attachment medium to facilitate binding to the repellent. Alternatively, the second-applied cells can be cells that naturally adhere to a component of the repellent; for example, fibroblasts will naturally adhere to hyaluronic acid. This method thus exploits differences in selectivity exhibited by the two cell types. Relative to fibroblasts, hepatocytes are selective in their ability to adhere to surfaces. Fibroblasts are generally promiscuous in their ability to bind to surfaces, and thus typically will serve as the second cell type in this variation of invention.

In a variation of these methods for producing micropatterned co-cultures, cells of one of the cell types (typically the first cell type) is genetically engineered using conventional techniques to produce a desired gene product that acts upon cells of a second cell type. For example, the first cell type can enable the second cell type to reproduce and grow, or signal the cells to express other functionality, such as causing the cells to divide more frequently (e.g., by expressing a growth factor) or undergo apoptosis (e.g., by expressing an ICE gene). For example, 3T3-Ras cells, which express basic fibroblast growth factor, can be co-cultivated with keratinocytes to induce the keratinocytes to grow faster.

By using micropatterning techniques, such as those described herein, the first and second cell types define a micropattern (i.e., are configured into a pattern having a resolution on a micron scale). In the micropattern of the co-culture, cells of either the first or second cell type are surrounded by (i.e., substantially (>95%), though not necessarily completely, enclosed by) cells of either the second or first cell type, respectively. For example, the cells of the co-culture can be configured such that "islands" of hepatocytes (cells of a first cell type) are surrounded by fibroblasts (cells of a second cell type). Such islands need not be perfectly circular in shape. For, example, the islands can be produced as stripes or rectangles. Regardless of the shape of the island, the spatial configuration that provides optimal growth conditions can readily be determined. In general, and when hepatocytes and fibroblasts are co-cultured for example, it is preferred that at least 30% of the cells of the island are within 100 $\mu$m of an interface between the island of cells (e.g., hepatocytes) and the surrounding cells (e.g., fibroblasts). More preferably, at least 50%, 80%, or 90% of the cells of the island are within 100 $\mu$m of the interface. Where the island is essentially circular, the island typically will have a diameter of 25–1,000 $\mu$m (preferably, 30–500 $\mu$m (or 100–500 $\mu$m)).

In a variation of the above methods, the invention provides a method for upregulating a metabolic or synthetic function of a cell of a first cell type; the method entails:

i) providing a protein-coated substrate, wherein a protein coating the substrate defines a micropattern on the substrate;

ii) contacting the protein-coated substrate with cells of a first cell type suspended in a first cell medium under conditions such that cells of the first cell type bind the protein of the protein-coated substrate, thereby producing a micropatterned cell-coated substrate; and iii) contacting the micropatterned cell-coated substrate with cells of a second cell type suspended in a second cell medium under conditions such that cells of the second cell type bind the substrate, thereby producing the micropatterned co-culture, wherein:

a) one of the cell media is a selective medium and one of the cell media is an attachment medium; and b) the cells of the first and second cell types define a micropattern wherein cells of the second cell type surround cells of the first cell type, and at least 30% of the cells of the first cell type are within 100 μm of an interface between the cells of the first cell type and the cells of the second cell type, thereby producing a micropatterned co-culture, wherein a metabolic or synthetic function of a cell of the first cell type is upregulated relative to cells of the first cell type in an unpatterned co-culture that comprises cells of the first and second cell types.

This method derives from the observation that, by using micropatterning techniques to modulate the level of heterotypic cell-cell contact in a co-culture, it is possible to upregulate a synthetic or metabolic function of a cell in the co-culture. For example, DNA synthesis, mRNA synthesis, and/or protein synthesis can be upregulated with this micropatterning method. In a micropatterned co-culture where islands of hepatocytes are surrounded by fibroblasts, the upregulation of cell function can be detected as an increase in intracellular or secreted albumin of a hepatocyte. Alternatively, or in addition, upregulation of cell function can be detected as an increase in urea synthesis in a hepatocyte.

As in the above-described methods for co-cultivating cells in a micropatterned configuration, examples of suitable combinations of cells for the co-culture include, without limitation, a) hepatocytes (e.g., primary hepatocytes) and fibroblasts (e.g., NIH 3T3-J2 cells);

b) hepatocytes and at least one other cell type, particularly liver cells, such as Kupffer cells, Ito cells, endothelial cells, and biliary ductal cells;

c) endothelial cells and smooth muscle cells;

d) tumorigenic parenchymal cells and mesenchymal cells;

e) hematopoietic cells and bone marrow cells (e.g., adipocytes, fibroblasts); and f) skin cells (e.g., keratinocytes) and fibroblasts.

Referring to the above list, the invention typically will be practiced such that an island of the first-named cell type in each of these combinations is surrounded by cells of the second-named cell type, and the function of the first-named cell type is upregulated. In producing the micropatterned co-culture, it is not necessary to adhere to the substrate the cells in which cell function will be upregulated prior to adhering the other cells. However, when producing a co-culture of hepatocytes and fibroblasts, the hepatocytes typically will be adhered to the protein-coated substrate prior to contacting the substrate with the fibroblasts. Other parameters of this aspect of the invention (e.g., island size, attachment factors, substrate, etc.) are essentially as described above.

Typically, the metabolic and/or synthetic function of cells of the first cell type is modulated at least 1.5-fold in micropatterned co-cultures, relative to a metabolic or synthetic function of cells of the first cell type in an unpatterned co-culture. As shown by the experiments described below, a change of at least 5-10-fold also is achievable. To detect the modulation of a metabolic or synthetic function, conventional molecular and biochemical assays can be used, such as those described below.

In practicing this method, not only is cell function upregulated to a higher absolute level (e.g., of albumin production) in the micropatterned co-cultures (relative to unpatterned co-cultures), but also the kinetics of this upregulation are increased. In other words, the rate at which a metabolic or synthetic function is upregulated to a particular level in the micropatterned co-culture is increased relative to the rate at which a metabolic or synthetic function is upregulated in an unpatterned co-culture. Thus, the invention also provides a method for modulating the kinetics at which metabolic or synthetic functions of a cell are upregulated in a co-culture. From a bioengineering perspective, this increase in the kinetic of cell function upregulation is advantageous, since it decreases the cultivation time needed for cells to reach a particular level of metabolic or synthetic function. In practice, an unpatterned co-culture may take 1–2 weeks to reach a particular level of cell function, whereas a micropatterned co-culture could be upregulated to that level in a single day.

Also included within the invention are the micropatterned co-cultures produced according to the methods described herein. Such micropatterned co-cultures of cells can be used as bioartificial organs for in vivo, ex vivo, or in vitro purposes. For example, a micropatterned co-culture of hepatocytes combined with fibroblasts can be used as an implantable (in vivo) or extracorporeal (ex vivo) artificial liver for replacement of liver function (e.g., in response to diseases, infections, or trauma), or in in vitro assays of liver function (for example, for toxicology or basic research purposes). Similarly, such micropatterned co-cultures can be used as a bioreactor or as a means to manufacture peptide compounds such as protein, enzymes, or hormones (e.g., albumin or clotting factors produced from hepatocytes). In this regard, the invention provides an advantage over cell-free methods of producing proteins, because intracellular post-translational modifications that occur in the co-cultures of the invention will provide a properly modified (e.g., glycosylated) protein.

As used herein, the term "micropattern" refers to a pattern formed on a substrate (e.g., by a protein, cell, or combination of cells of two or more types), which has a spatial resolution (e.g., 1–5 μm) that permits spatially controlling cell placement at the single-cell level. Thus, using micropatterning methods, one can precisely manipulate cell-cell interactions. In contrast, in an "unpatterned" co-culture of cells, the cells are randomly distributed.

As used herein, an "island" of cells is a single cell, or typically a group of cells, of one cell type that is surrounded by cells of another cell type (e.g., a group of hepatocytes surrounded by fibroblasts). Thus, an interface is formed where cells at the periphery of the island meet the surrounding cells. An island need not be circular in shape; for example, rectangular islands, and islands of other, amorphous shapes can be used in the invention. The size of the island can be adjusted to provide optimal growth conditions for the particular combination of cells in the co-culture. For example, for islands of hepatocytes surrounded by fibroblasts, at least 30% (preferably at least 50%, 80%, or 90%) of the cells in the island typically are within 100 μm from an interface between the cell types. Thus, where the island is essentially circular in shape, islands that are less than 1,000 μm in diameter are suitable. Typically, the island will be 30–500 μm in diameter.

DETAILED DESCRIPTION

The working examples are provided to illustrate, not limit, the invention. Various parameters of the scientific methods employed in these examples are described in detail below and provide guidance for practicing the invention in general.

In these particular working examples, hepatocytes are co-cultured with fibroblasts; as is described herein, similar methods can be used to co-culture other combinations of cells. These experiments demonstrate that two cell types can be co-cultured in a micropattern configuration. In other words, the two cell types can be used to define a pattern having a resolution on a micron scale. These experiments also show that, by using micropatterning to optimize the extent of heterotypic cell-cell contacts in the co-culture, the metabolic and synthetic functions of cells of the micropatterned co-culture are upregulated relative to cells in an unpatterned configuration.

PART I

Materials And Methods

Figure 1:
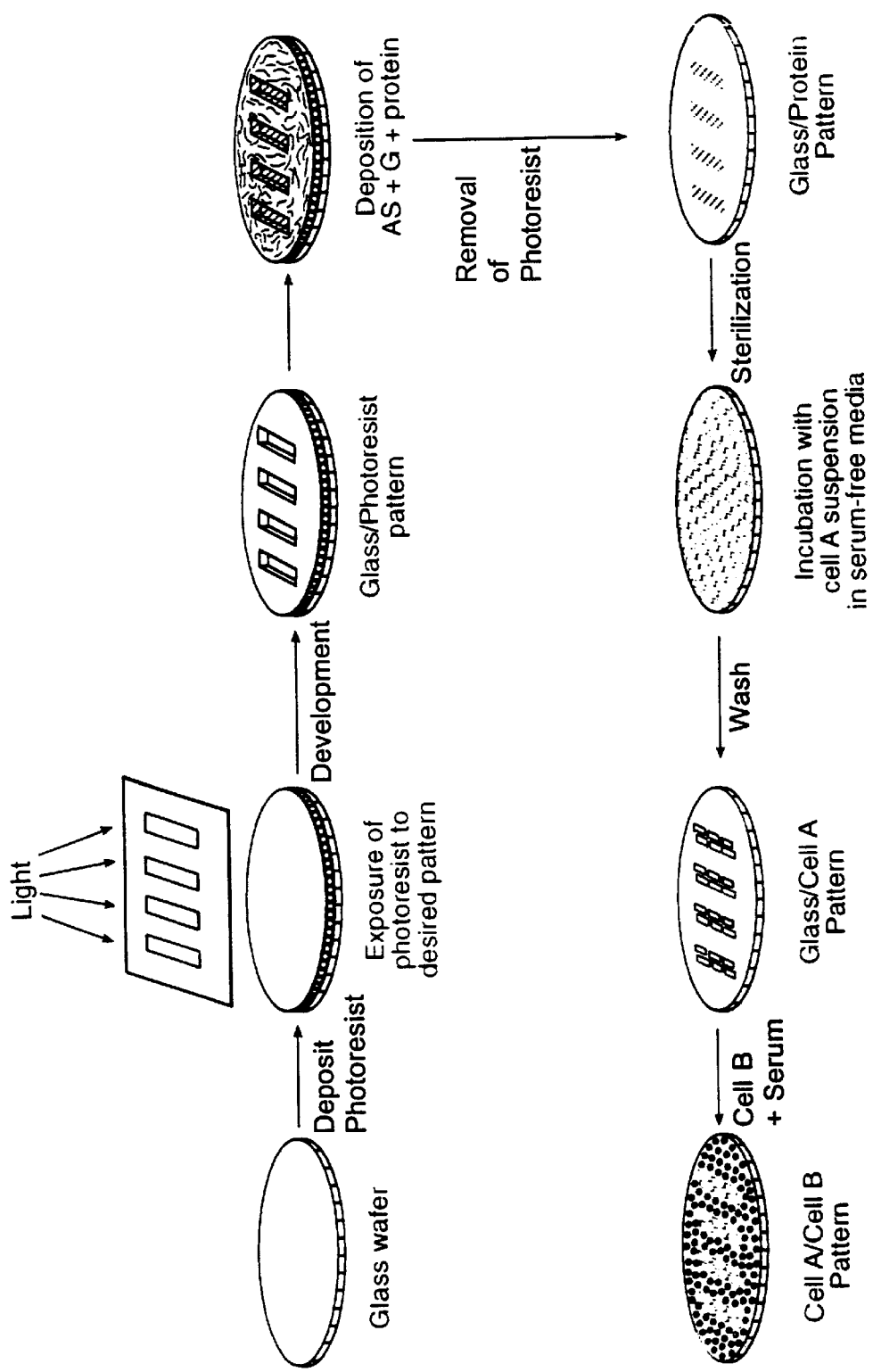
FIG. 1 is a schematic representation of a process to generate micropatterned co-cultures.

Microfabrication techniques were used to modify glass substrates with biomolecules. These modified substrates were utilized to pattern a single cell type or micropattern co-cultures in various configurations. FIG. 1 schematically depicts the overall process for producing micropatterned co-cultures.

Microfabrication Of Substrates

The experimental substrates were produced utilizing standard microfabrication techniques. Chrome masks of the desired dimensions were generated on a pattern generator (Gyrex), which transferred the pattern to a chromium coated quartz plate using a contact printer and a developer. Round, 2" diameter×0.02" thickness borosilicate wafers (Erie Scientific) were cleaned in a piranha solution (3:1 $H_2SO_4$: 30% $H_2O_2$) for 10 minutes, rinsed, and blown dry with a $N_2$ gun. Wafers were then dehydrated by baking for 60 minutes at 200° C. Discs were subsequently coated with positive photoresist (OCG 820–27 centistokes) on a Headway spin-coater with vacuum chuck as follows: dispense photoresist at 500 RPM for 2 seconds, spread photoresist at 750 RPM for 6 seconds, spin at 4000 RPM for 30 seconds, resulting in a 1 $\mu$m coating (Step A, FIG. 1). Wafers were then pre-baked for 5 minutes at 90° C. to remove residual solvent and anneal any stress in the film. Wafers were exposed in a Bottom Side Mask Aligner (Karl Suss) to ultraviolet light through the desired chromium mask to create a latent image in the resist layer. Exposure occurred under vacuum-enhanced contact for 3 seconds. Exposed photoresist was then developed to produce the final three-dimensional relief image for 70 seconds in developer (OCG 934 1:1), rinsed three times under running deionized water and cascade rinsed for 2 minutes (Step B, FIG. 1). Subsequently, discs were hard-baked for 30 minutes at 120° C. to remove residual developing solvents and promote adhesion of the film. Finally, substrates were exposed to oxygen plasma at 250 W for 4 minutes to remove unwanted resist in areas to be subsequently modified. Wafers were stored at room temperature for up to 2 months. Substrates were subsequently re-exposed to oxygen plasma 24 hours prior to further processing to ensure availability of borosilicate for surface modification on a Plasma Day Etcher at a base vacuum of 50 mTorr and $O_2$ pressure of 100 mTorr at a power of 100 W for 2–4 minutes.

Surface Modification Of Substrates

Substrates were modified using experimental methods similar to those developed by Lom et al. and Britland et al. (Step C, FIG. 1) (Stenger et al., 1992, J. American Chemical Society 114:8345–8442; Lom et al., 1993, J. Neurosci. Methods 50:385–397). Briefly, substrates were rinsed twice in distilled, deionized (DD) water and allowed to air dry. Silane immobilization onto exposed glass was performed by immersing samples for 30 seconds in freshly prepared, 2% v/v solution of 3-[(2-aminoethyl)amino] propyltrimethoxysilane (AS, Hüls America) in water followed by 2 rinses in 200 mL DD water. Wafers were then dried with nitrogen gas and baked at 120° C. for 10 minutes. Next, discs were immersed in 20 mL of 2.5% v/v solution of glutaraldehyde in PBS (pH 7.4) for 1 hour at 25° C. Substrates were then rinsed twice in fresh PBS, and immersed in a 4 mL solution of a 1:1 solution of 1 mg/mL collagen I (Dunn et al., 1991, Biotechnology Progress 7:237–245): DD water for 15 minutes at 25° C. Discs were subsequently immersed in acetone and placed in a bath sonicator (Bransonic) for 15 minutes to remove residual photoresist ultrasonically (Step D, FIG. 1). Wafers were then rinsed twice in DD water, and soaked overnight in 70% ethanol for sterilization (Step E, FIG. 1).

Surface Characterization Of Substrates

Autofluorescence

Wafers were observed using a Nikon Diaphot microscope equipped with a Hg lamp and power supply (Nikon). The autofluorescence of photoresist (excitation: 550 nm, emission: 575 nm) was used to visualize micropatterned substrates prior to surface modification. Absence of autofluorescence after sonication was taken to indicate removal.

Profilometry

Profilometry was performed to characterize surface topology on a Dektak 3 Profilometer (Veeco Instruments) with a 12.5 $\mu$m radius probe at a scan rate of 100 $\mu$m/s.

Atomic Force Microscopy (AFM)

AFM was performed in order to characterize the spatial distribution of immobilized groups. AFM was performed with a Nanoscope 3 (Digital Instruments) equipped with a standard 117 $\mu$m silicon cantilever operating in tapping mode with a scan size of 100 $\mu$m.

Indirect Immunofluorescence Of Collagen I

Collagen-derivatized substrates were incubated at 37° C. with undiluted Rabbit Anti-Rat Collagen I Antisera (Biosciences) by inverting substrates onto parafilm that contained a droplet (50 $\mu$L) of antisera for 1 hour. Substrates were then washed thoroughly in PBS and placed on a rotating shaker at 25° C. for 30 minutes. This washing procedure was repeated twice. Next, discs were inverted onto parafilm with 50 $\mu$L (1:20) of Dichlorotriazinylamino Fluorescein (DTAF)-conjugated Donkey Anti-Rabbit IgG (Jackson) in blocking solution. Blocking solution consisted of 3% w/w bovine serum albumin, 1% donkey serum, 0.04% sodium azide, pH 7.4. Finally, substrates were washed in PBS overnight, and observed by fluorescence microscopy (excitation: 470 nm, emission: 510 nm).

Cell Culture

Hepatocyte Isolation and Culture

Hepatocytes were isolated from 2- to 3-month-old adult female Lewis rats (Charles River) weighing 180–200 g (Seglen et al., 1976, Methods in Biol. 13:29–83; Dunn et al., 1989, FASEB J. 3:174–177). Routinely, 200–300 million cells were isolated with viability between 85% and 95%, as judged by Trypan blue exclusion. Non-parenchymal cells, as judged by their size (<10 μm in diameter) and morphology (nonpolygonal or stellate), were less than one percent. Culture medium was Dulbecco's modified Eagle's Medium (DMEM, Gibco) supplemented with 10% fetal bovine serum (FBS, JR Scientific), 0.5 U/mL insulin, 7 ng/mL glucagon, 20 ng/mL epidermal growth factor, 7.5 (g/mL hydrocortisone, 200 U/mL penicillin, 200 (g/mL streptomycin and 50 (g/mL gentamycin ('hepatocyte media with serum'). Serum-free culture medium was identical except for the inclusion of 40 (g/mL of L-Proline (Sigma) and exclusion of FBS (Lee et al., 1993, Biomaterials 14:12) ('serum-free hepatocyte media').

NIH 3T3-J2 Culture

NIH 3T3-J2 cells, grown to pre-confluence, were trypsinized in 0.01% trypsin (ICN Biomedicals)/0.01% EDTA (Boehringer Mannheim) solution in PBS for 5 minutes and then resuspended in 25 mL media. Approximately 10% of the cells were inoculated into a fresh tissue culture flask. Cells were passaged at pre-confluency no more than 12 times. Cells were cultured in 75 $cm^3$ flasks (Corning) at 10% $CO_2$, balance moist air. Culture medium consisted of DMEM (Gibco) with high glucose, supplemented with 10% bovine calf serum (BCS, JRH Biosciences) and 200 U/mL penicillin and 200 μg/mL streptomycin.

Cell Culture on Modified Surfaces

Wafers were rinsed in sterile water, and incubated in 0.05% w/w bovine serum albumin in water at 37(C for 1 hour to pre-coat substrates with a non-adhesive protein. Substrates were then washed twice with serum-free media. Next, hepatocytes were seeded at high density ($4\times10^6$/mL) in serum-free media for 1.5 hours at 37° C., 10% $CO_2$, balance air (Step E, FIG. 1). Surfaces were then rinsed twice by pipetting and then aspirating 4 mL of serum-free media, re-seeded with hepatocytes for 1.5 hours, rinsed with 4 mL of serum-free media, and incubated overnight (Step F, FIG. 1). The following day, 3T3 cells were trypsinized as described above, counted with a hemocytometer and plated at $1\times10^6$/mL in 2 mL of serum-containing, high glucose DMEM, and allowed to attach overnight (Step G, FIG. 1).

'Randomly-distributed' (i.e., unpatterned) co-cultures consisted of hepatocyte seeding in the desired number (usually 250,000) on a uniformly collagen-derivatized surface followed by 3T3 seeding after 24 hours.

Immunofluorescent Staining

Cultures were washed 2 times with 2 mL PBS, fixed and permeabilized with 10 mL of acetone at −20° C. for 2 minutes, and washed twice in 10 mL PBS. Cultures on wafers were incubated at 37° C. with undiluted Rabbit Anti-Rat Pan Cytokeratin Antisera (Accurate Chemical), by inverting substrates onto parafilm containing a 50 μL droplet of antisera for 1 hour. Substrates were then washed, incubated with secondary antibody, and washed (as described above for indirect immunofluorescence of collagen). Secondary antibody also included rhodamine-phalloidin (1:100, Molecular Probes) for fluorescent labeling of F-actin. Specimens were observed and recorded using a Nikon Diaphot microscope (Nikon) equipped with a Hg lamp and power supply (Nikon), light shuttering system (Uniblitz D122), CCD camera (Optitronics CCD V1470), and MetaMorph Image Analysis System (Universal Imaging) for digital image acquisition.

Image Analysis

To quantitatively describe the extent of heterotypic interactions, the fraction of cell perimeter in contact with adjacent cells of a different cell type (X) was measured. For example, X=1 for a single cell island whereas X=0 for a cell amidst hepatocyte neighbors. Images were acquired as described above and analyzed with MetaMorph Image Analysis System. Cells were sampled from each field and manually outlined to obtain individual cell perimeters, P. Subsequently, the regions of heterotypic cell-cell contact were similarly delineated, F. Each cell was assigned its characteristic X=F/P and these values of X were averaged over 20–50 cells for each condition. For population distributions, individual values of X were assigned to an appropriate 'bin', and histograms were generated.

RESULTS

As is discussed below, surface characterization studies on substrates in the absence of cells were first performed to first exemplify spatially-defined surface chemistries. Subsequently, the ability to micropattern single cell cultures and co-cultures including two different cell types was shown, as is described below.

Surface Characterization

Topological and spatial uniformity of photoresist patterns were assessed using profilometry and autofluorescent properties of photoresist. The photoresist coating was approximately 1.35 μm thick, as determined using the specified spin-coating parameters. Furthermore, the thickness of photoresist varied <5% within each scan. Autofluorescence of photoresist was utilized to examine integrity and distribution of photoresist prior to and during processing. Autofluorescent regions corresponding to ~1 μm variations in thickness were detected. Absence of any contaminant fluorescence in the dark lanes indicates complete, uniform removal of exposed photoresist during development.

To demonstrate regional aminosilane (AS) modification of borosilicate, substrates were exposed to AS, followed by removal of photoresist. Aminosilane modification has been previously reported to modify the three-phase contact angle of water with the surface (Lom et al., 1993, J. Neurosci. Methods 50:385–397); therefore, the perimeter of a single water droplet was used to display microscopic undulations on patterns of varying hydrophilicity. These undulations were observed; 20 μm AS modified lanes exhibit differential wetting properties relative to the adjacent 50 μm unmodified lanes. Therefore, selective AS modification of exposed glass was demonstrated in the pattern of the original 20 μm/50 μm striped photoresist pattern, indicating that photoresist can serve as a 'chemical mask' to AS modification of underlying glass.

Collagen Immobilization Via Glutaraldehyde Derivatization Of Patterned AS Surfaces Was Also Characterized Fluorescence micrographs were obtained, showing the results of indirect immunofluorescent staining of areas of presumed collagen immobilization. Fluorescent regions, corresponding to regions of collagen localization, were patterned uniformly with spatial resolution on the micron level. Furthermore, fluorescent patterns corresponded to initial photoresist patterns without evidence of undercutting. Despite processing in acetone and 70% ethanol, collagen retained sufficient immunoreactivity for antibody binding.

Collagen-derivatized surfaces were also analyzed with AFM to determine differences in topology between unmodified and modified borosilicate. Modified regions with a width of 20 μm were found to have an average height of 4 nm above the unmodified, 50 μm lanes. These data can be utilized to approximate the number of collagen monolayers atop AS.

Micropatterning Of Co-Cultures

The aforementioned experiments demonstrate the ability to reproducibly utilize photoresist patterns to generate immobilized collagen patterns; the following experiments illustrate the applicability of these techniques to cellular micropatterning. Seeding of the first cell type, hepatocytes, resulted in localization to collagen-derivatized regions and normal polygonal morphology. The cellular configurations were dictated by the positioning of collagen on glass, the pattern of which was in turn controlled by the choice of chromium mask in the microfabrication procedure. In addition, hepatocytes conformed to the edges of the collagen pattern on the modified glass. The typical hepatocyte diameter in suspension is 20 $\mu$m, whereas, upon attachment and unconstrained spreading, cell diameters increase to 30–40 microns. Therefore, after attachment to 20 $\mu$m lines, cells elongated in the axial direction upon spreading. Similar cytoskeletal changes were observed in cells on corners of larger patterns or on the perimeter of circular patterns.

The versatility of this technique was seen in phase-contrast micrographs. Initial hepatocyte patterns of 20 $\mu$m and 200 $\mu$m were modified by the addition of fibroblasts in serum-containing media. Fibroblasts localized solely to unmodified (glass) regions of patterned substrates resulting in micropatterned co-cultures of 20 $\mu$m/50 $\mu$m and 200 $\mu$m/500 $\mu$m. This approach is adaptable to both micropatterning of single cell cultures and co-cultures of two different cell types.

Spreading of the primary cell type typically resulted in negligible residual sites of collagen-derivatization. Therefore, attachment of the secondary cell type is limited either to unmodified glass or the surface of the primary cell type. 3T3 fibroblasts do not undergo significant attachment to hepatocyte surfaces, as shown in plating experiments of fibroblasts on monolayers of hepatocytes which showed no attachment even after a 4 hour incubation (data not shown). In addition, fibroblast attachment and spreading on glass was characterized by seeding cells in serum-containing media on glass coverslips where they attached and spread with high efficiency within 4 hours (data not shown).

Indirect immunofluorescence was used to stain selectively cell populations and aid in visual discrimination between different cell types. The presence of cytokeratin, an intermediate filament expressed in hepatocytes but absent in mesenchymal cells, was compared with F-actin, a cytoskeletal protein present in all mammalian cells. A patterned co-culture of 200 $\mu$m/500 $\mu$m was also compared with a 'randomly distributed' co-culture with identical attached cell numbers of both cell populations. The level of homotypic hepatocyte interaction in a 200 $\mu$m stripe of micropatterned cells was compared with the level in a random distribution of cells. Hepatocytes in the 200 $\mu$m stripe had primarily homotypic contacts, whereas those in the random distribution had predominantly heterotypic contacts. Furthermore, the distribution of heterotypic interaction over the patterned cell population was greatly reduced over that of random co-cultures, where hepatocytes were present in single cell islands, doublets, and triplets.

Figure 2:
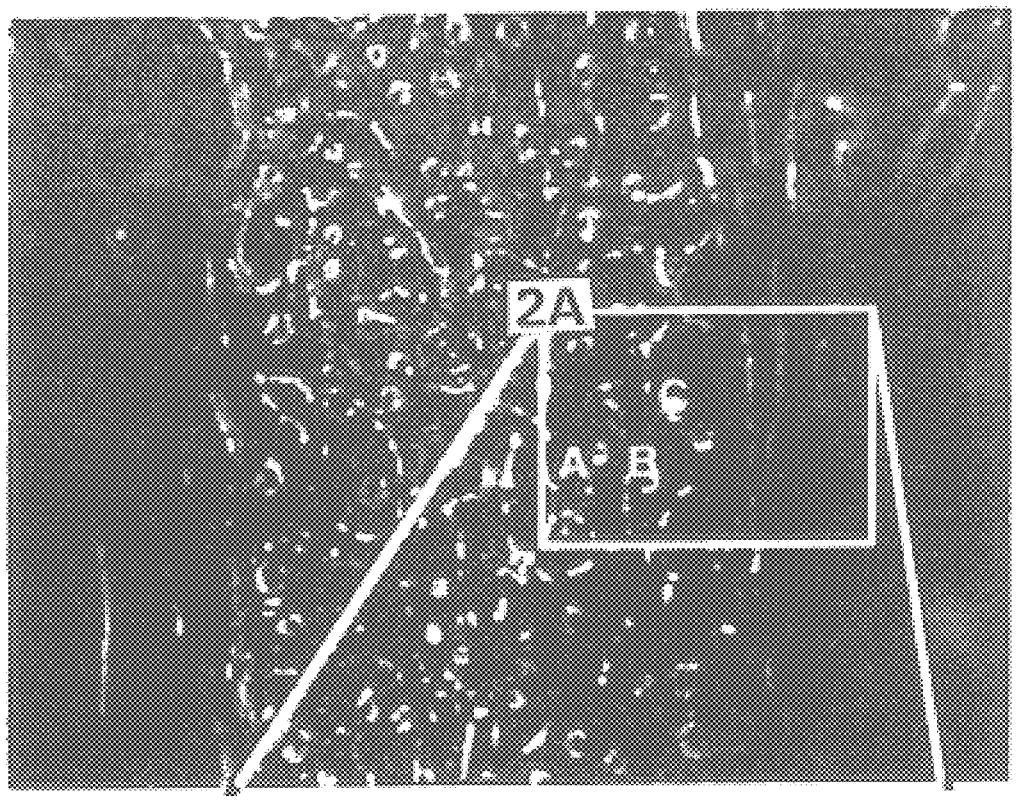
FIGS. 2 and 2A are schematic representations of a method for determining X, the heterotypic interaction parameter.
Figure 2A:
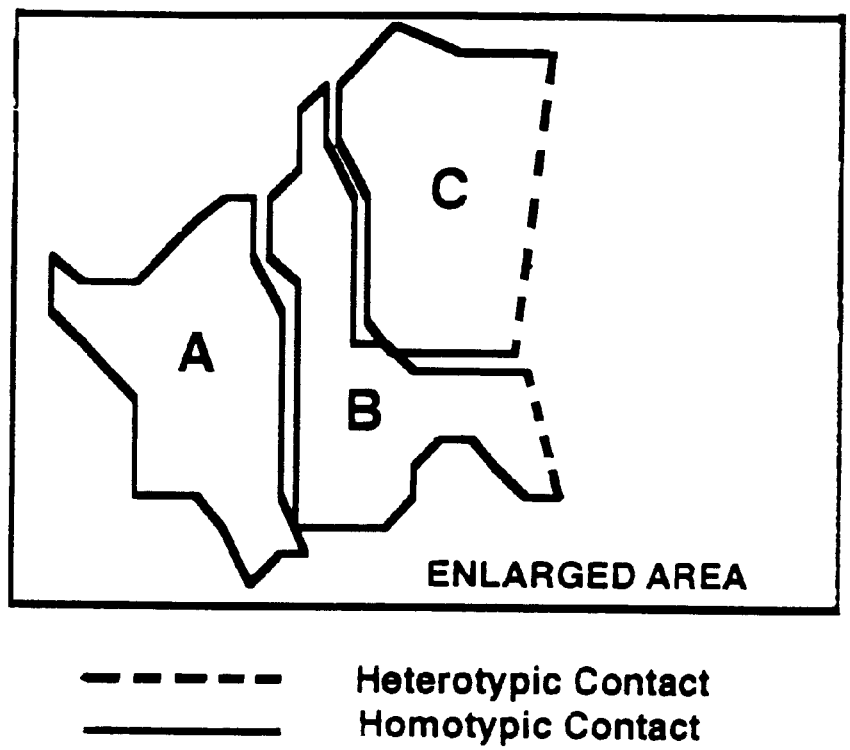

To describe quantitatively the extent of heterotypic contact, image analysis and perimeter tracing were used to define the fractional cell perimeter engaged in heterotypic cell contact as X, as described above. FIG. 2 schematically depicts sample perimeter tracings (black lines) with highlighted interfaces of heterotypic contacts corresponding to hepatocytes in a digitally-acquired phase micrograph. This particular pattern (200 $\mu$m/500 $\mu$m) has very little heterotypic contact, as was visually observed; therefore, the average X over the population is small due to the majority of cells with X=0. The mean value of X over a cell population can be changed from 0.7 in the randomly distributed culture to 0.08 using micropatterning. Moreover, different patterns (20/50) produce distinct mean values of X (X=0.55). Variations of X from the mean were also examined for randomly distributed cultures as compared to defined patterns (20/50). As observed microscopically, hepatocytes in randomly distributed cultures experience heterogeneous microenvironments—single hepatocytes, doublets, and multicellular aggregates can be observed within a given culture. Quantitative analysis of population distributions corroborate the variability in X in randomly distributed cultures as compared to micropatterns (20/50 and 50/50), which exhibited a relatively small variance around the mean value of X. Thus, variations in cellular microenvironment, both in amount and variability, were achieved without varying the numbers of cells in each sub-population.

DISCUSSION

Many conventional co-culture systems have been limited by the inability to vary local cell seeding density independently of the cell number, as well as inherent variations in the distribution of cell contacts over a population of cells. The invention provides a versatile technique for the micropatterning of two different cell types derived from conventional strategies for surface modification with aminosilanes linked to biomolecules and by manipulating the serum content of cell culture media, as described above. This co-culture technique allows the manipulation of the initial cellular microenvironment without variation of adhered cell number. Specifically, it was possible to control both the degree and type of initial cell-cell contact. Differences in homotypic and heterotypic interaction were demonstrated, allowing variations in exposure to cell-surface receptors, locally secreted extracellular matrix, and local concentrations of soluble factors.

In these patterning methods AS was applied after photoresist patterning but before photoresist lift off. The integrity of the photoresist was preserved throughout the surface modification process and removed the photoresist after the deposition of collagen. This was achieved by deposition of AS in water, which does not normally attack photoresist. AS is known to oligomerize in aqueous solution (Arkles et al., 1991, Hüls America, N. J., 65–73), but is stable at least for a period of hours. In this way, photoresist was used to mask the borosilicate from non-specific protein adsorption and it was not necessary to rely on protein denaturation and desorption or on AS deposition prior to photoresist patterning.

Atomic force microscopy was utilized to approximate the depth of the immobilized collagen layer. Modified regions were ~4 nm above the unmodified regions. AS molecules have been estimated to have a height of 1.2 nm end-to-end (Lom et al., 1993, J. Neurosci. Methods 50:385–397). In the helical configuration, collagen I fibrils have dimensions of 300 nm in length and 1.2 nm in diameter (Darnell et al., 1990, Molecular Cell Biology, 904–905). These data suggest that there were 1–2 layers of collagen fibrils, configured lengthwise, corresponding to an upper limit of 0.1 $\mu$g/cm$^2$ per monolayer of 'side-on' packed fibrils (Deyme et al., 1986, J. Biomedical Materials Research 20:39–45). Therefore, achievable collagen surface concentrations are within an order of magnitude those observed in adsorbed collagen systems (0.37 $\mu$g/cm$^2$) (Deyme et al., 1986, J. Biomedical Materials Research 20:39–45). Another consideration is the bioactivity of biomolecules after exposure to acetone and ethanol. The preservation of bioactivity of collagen I via cell attachment and spreading as well as by antibody binding for indirect immunofluorescence has now been demonstrated. Proteins sensitive to acetone may benefit from adaptation of the photoresist lift-off procedure.

Using primary rat hepatocytes and 3T3 fibroblasts, the initial heterotypic (X) interactions were varied over a wide range while preserving the ratio of cell populations in culture. Thus, co-culture interactions now can be manipulated in an entirely new dimension. If desired, three-phase co-cultures can be established by patterning of two different, cell-specific biomolecules. The micropatterned co-cultures had less variation in the level of heterotypic contacts (X) than did random co-cultures. Therefore, measurement of macroscopic biochemical quantities in micropatterned co-cultures will provide better representations of specific cell-cell interactions than those seen in unpatterned co-cultures.

SUMMARY

The invention provides a simple, versatile technique for controlling homotypic versus heterotypic interactions of at least two cell types in culture. One can vary X without changing the number of cells in each sub-population and therefore vary the ratio of cell types in a given culture.

PART II

The following experiments demonstrate that the methods of the invention can be used to upregulate metabolic and/or synthetic functions (e.g., liver-specific functions) of cells in the micropatterned co-culture.

MATERIALS AND METHODS

Substrates for micropattern formation were prepared essentially as described above.

Hepatocyte Isolation And Culture

Hepatocytes were isolated from 2- to 3-month-old adult female Lewis rats (Charles River Laboratories, Wilmington, Mass.) weighing 180–200 g, by a modified procedure of Seglen (1976). Detailed procedures for isolation and purification of hepatocytes were previously described by Dunn et al (FASEB, 1989). Routinely, 200–300 million cells were isolated with viability between 85% and 95%, as judged by trypan blue exclusion. Nonparenchymal cells, as judged by their size (<10 μm in diameter) and morphology (nonpolygonal or stellate), were less than 1%. Culture medium was Dulbecco's modified eagle's medium (DMEM, Gibco) supplemented with 10% fetal bovine serum (FBS, Sigma, St. Louis, Mo.), 0.5 U/mL insulin, 7 ng/mL glucagon, 20 ng/mL epidermal growth factor, 7.5 mg/mL hydrocortisone, 200 U/mL penicillin, and 200 mg/mL streptomycin ('hepatocyte media with serum'). Serum-free culture medium was identical except for the exclusion of FBS.

NIH 3T3-J2 Culture

NIH 3T3-J2 cells were provided by Howard Green (Harvard Medical School). Cells grown to preconfluence were passaged by trypsinization in 0.01% trypsin (ICN Biomedicals, Costa Mesa, Calif.)/0.01% EDTA (Boehringer Mannheim, Indianapolis, Ind.) solution in PBS for 5 minutes, diluted, and then inoculated into a fresh tissue culture flask. Cells were passaged at pre-confluency no more than 10 times. Cells were cultured in 175 cm$^2$ flasks (Fisher, Springfield, N.J.) at 10% $CO_2$, balance moist air. Culture medium consisted of DMEM (Gibco, Grand Island, N.Y.) with high glucose, supplemented with 10% bovine calf serum (BCS, JRH Biosciences, Lenexa, Kans.) and 200 U/mL penicillin and 200 mg/mL streptomycin ('fibroblast media'). In some cases, growth arrested cells were obtained for DNA analysis by incubation with 10 mg/mL mitomycin C (Boehringer Mannheim) in media for 2 hours (reconstituted just prior to use) followed by three washes with media. Mitomycin C-treated fibroblasts were shown to have constant levels of DNA for 10 days of culture, verifying the lack of fibroblast growth under these conditions.

Cell Culture On Modified Surfaces

Wafers were sterilized by soaking for 2 hours in 70% ethanol in water at room temperature. Subsequently, wafers were rinsed in sterile water and incubated in 0.05% w/w bovine serum albumin (BSA) in water at 37° C. for 1 hour to precoat substrates with a nonadhesive protein. Substrates were then placed in sterile P-60 tissue culture dishes (Corning, Corning, N.Y.), and rinsed in sterile water followed by a final rinse with serum-free media. Next, hepatocytes were seeded at high density (1–2×10$^6$/mL) in 2 mL serum-free media for 1.5 hours at 37° C., 10% $CO_2$, balance air followed by two rinses with serum-free media. This process was repeated twice to ensure confluence of hepatocytes, especially on larger dimension patterns. The following day, 3T3 cells were trypsinized as described above, counted with a hemocytometer, plated at 3.75×10$^5$/mL in 2 mL of serum-containing, high-glucose DMEM, and allowed to attach overnight. Subsequently, 2 mL hepatocyte culture media (described above) was sampled and replenished daily.

Experimental Design

Spatial configurations of micropatterned co-cultures were manipulated by varying mask dimensions. Transparent circular areas (or 'holes') on chrome masks correspond to derivatized, and ultimately hepatocyte-adhesive, areas of glass substrates. In order to achieve identical hepatocyte numbers across varying micropatterned configurations, the total surface area of all 'holes' was kept constant across all masks despite changes in hole diameter and center-to-center spacing. All arrays were hexagonally packed with the exception of the largest dimension hole which consisted of a single unit of 17800 μm diameter. Thus, pattern dimensions varied as follows (hole diameter (in microns), center-to-center spacing (in microns)): 36, 90; 100, 250; 490, 1229; 6800, 16900; and a single unit of 17800 μm diameter, where the resulting total hepatocyte-adhesive area on 2" diameter glass substrates would be identical in all cases.

Analytical Assays

Media samples were collected daily and stored at 4° C. for subsequent analysis for urea and albumin content. Urea synthesis was assayed using a commercially available kit (Sigma Chemical Co., kit No. 535-A). Reaction with diacetyl monoxime under acid and heat yields a color change detected at 540 nm. Albumin content was measured by enzyme-linked immunosorbent assays (ELISA) as described previously (Dunn et al., 1991, Biotechnology Progress 7:237–245). Rat albumin and anti-rat albumin antibodies were purchased from Cappel Laboratories (Cochranville, Pa.).

DNA analysis was adapted from a method of MacDonald and Pitt (1991). Cells were sacrificed at the indicated time of culture by washing with PBS, removal and immersion of wafer into PBS to eliminate dead cells underneath the substrate, and subsequent incubation with 0.05% (w/v) type 4 collagenase (Sigma) in Kreb's Ringer Buffer at 37° C. for 30 minutes to release the cell layer from the underlying substrate. Next, cells were removed with a rubber policeman and the cell/collagenase mixture was removed. The substrate was washed with PBS which was then combined with the above solution. The resulting solution was combined with an equivalent volume of hepatocyte media for neutralization of collagenase, followed by centrifugation at 1000 RPM for 5 minutes. The supernatant was aspirated, and cells were resuspended in 2 mL PBS. Subsequently, the samples were frozen at −80° C. for up to 1 month.

For analysis, the frozen samples were rapidly thawed in a 37° C. water bath to promote membrane rupture. Freeze-thaw protocols have been established as an effective way to rupture the cell membrane in order to gain access to cellular contents. To ensure complete cell lysis, samples were then sonicated using a probe sonicator (Branson) for 10 seconds at 4° C. Samples were vortexed and 20 ml samples were placed into a 96-well plate (NUNC, Denmark). Similarly, 20 ml of DNA standard (double stranded Calf Thymus DNA, Sigma) in PBS from 100 to 0 mg/mL were vortexed and placed on each plate. This volume was combined with 100 ml salt/dye buffer (2 M NaCl, 10 mM Tris, 1 mM EDTA, 1.6 mM Hoechst 33258 (Molecular Probes, Eugene, Oreg.)). Samples and standards were allowed to incubate with salt/dye buffer at room temperature in the dark for 30 minutes before reading on a Spectrofluorometer (Millipore, Bedford, Mass.) Excitation 360 nm, ½ bandwidth 40 nm, Emission, 460 nm, ½ bandwidth 40 nm.

Analysis Of DNA Content

The total DNA content in cultures with growth-arrested fibroblasts was assayed as follows. Mitomycin C was utilized to growth arrest fibroblasts (as described above) and $1.5 \times 10^6$ fibroblasts were counted with a hemocytometer and added to micropatterned hepatocyte cultures. Replicate cultures were either sacrificed 6 hours after fibroblast seeding or after 9 days of co-culture and assayed for total DNA as described above.

Immunohistochemistry

Cultures were washed twice with PBS, fixed with 4% paraformaldehyde in PBS for 30 minutes, and permeabilized for 10 minutes with 0.1% Triton in PBS. Endogenous avidin-binding activity of hepatic tissue was blocked by 20 minute incubations with 0.1% avidin and 0.01% biotin in 50 mM Tris-HCl respectively (Biotin Blocking System X590, DAKO, Carpinteria, Calif.). Endogenous peroxidase activity was blocked by 30 minute incubation with a hydroxgen peroxide and sodium azide solution (Peroxidase Blocking Reagent, DAKO). Rabbit anti-rat albumin antibodies (Cappell) were utilized with horse-radish peroxidase visualization by use of a biotinylated secondary antibody to rabbit IgG, streptavidin-labelled horse radish peroxidase, and hydrogen peroxide in the presence of 3-amino-9-ethylcarbazole as a substrate (Rabbit Primary Universal Peroxidase Kit #K684, DAKO).

Functional Bile Duct Staining

Cultures were washed three times with media and incubated for 5 hours with 2 $\mu$M Carboxyfluorescein diacetate (Molecular Probes) in an adapted method of LeCluyse et al. (1994). Subsequently, cultures were washed again three times and examined microscopically. Digital images were obtained on a Nikon Diaphot microscope equipped with Hg lamp and excited at 470 nm excitation and 510 nm emission.

Image Acquisition And Analysis

Specimens were observed and recorded using a Nikon Diaphot microscope equipped with a CCD camera (Optronics CCD V1470), and MetaMorph Image Analysis System (Universal Imaging, Westchester, Pa.) for digital image acquisition. Image analysis on immunostained images was performed utilizing the thresholding function in MetaMorph and visual correlation with brightfield images.

Statistics And Data Analysis

Experiments were repeated two to three times with duplicate or triplicate culture plates for each condition. Two duplicate wells were measured for biochemical analysis. One representative experiment is presented where the same trends were seen in multiple trials but absolute rates of production varied with each animal isolation. Each data point represents the mean of three dishes. Error bars represent standard error of the mean. Statistical significance was determined using one-way ANOVA (analysis of variance) on Statistica (StatSoft) with Tukey HSD (Honest Significant Difference) Post-Hoc analysis with $p<0.05$.

RESULTS

Micropatterned co-cultures were generated with variations in heterotypic interface but with identical surface area (i.e., cell numbers) dedicated to both hepatocyte and fibroblast adhesion. Five different configurations ranging from maximal heterotypic contact (smallest islands) to minimal heterotypic contact (single island) were characterized for expression of liver-specific function by use of: two biochemical markers (albumin and urea synthesis), immunohistochemistry (intracellular albumin staining), transport across apical surface (bile duct excretion), and DNA content. These results show that micropatterning can be used to optimize the degree of heterotypic interactions and thereby optimize cell function. In this case, an increase in heterotypic interactions is correlated with an increase in liver-specific functions.

Characterization Of Initial Cell Distribution

All 5 micropatterns were designed to have similar levels of hepatocyte-adhesive surface area (2.5 cm$^2$), which is expected to correspond to identical number of attached hepatocytes. Variations in spatial configurations were utilized to generate differences in total perimeter of hepatocyte islands from 5.6 cm to 2800 cm, which, upon addition of fibroblasts, generally correspond to variations in the total heterotypic interface. Micropatterns ranged from many single hepatocyte islands of 36 $\mu$m diameter to a single island of 17.8 mm diameter (100 $\mu$m, 490 $\mu$m, and 6800 $\mu$m islands also were detected). Micropatterned hepatocytes adhered predominantly to collagen-modified areas in all 5 conditions with close agreement between theoretical and observed values for total initial hepatocyte island perimeter (data not shown).

To verify similar numbers of attached hepatocytes across various spatial configurations, the DNA content of micropatterned hepatocyte cultures was measured 24 hours after hepatocyte seeding (i.e. prior to fibroblast seeding). All cultures had statistically similar levels of DNA (8±1.8 $\mu$g) with the exception of increased DNA content (18±3.3 $\mu$g) on the smallest island (36 $\mu$m diameter) micropatterns.

The smallest islands were designed to produce single cell islands. The dimensions of these islands (36 $\mu$m diameter) was chosen to correspond with the experimentally determined projected surface area of a single, spread hepatocyte on immobilized collagen I of 1000 $\mu$m$^2$ (data not shown); however, isolated rat hepatocytes have a diameter of approximately 20 $\mu$m, allowing the potential for individual islands to retain more than one hepatocyte upon seeding with a concentrated cell suspension. In addition, hepatocytes have been shown to have an increased mitotic index at low seeding densities (Nakamura et al., 1983, J. Biochemistry 94:1029–1035), which may have contributed to increased hepatocyte DNA in this condition. To distinguish between increased cell number as compared to increased ploidy, image analysis of one thousand 36 $\mu$m micropatterned islands was completed at 6 hours after initiation of cell seeding. This analyses demonstrated more than one cell per island in 57% of cases, with an average of 1.9±1.2 cells per island. Therefore, increased DNA was due to increased hepatocyte number on the smallest pattern.

Addition of 3T3-J2 fibroblasts to micropatterned hepatocytes resulted in micropatterned co-cultures with marked alterations in initial heterotypic interface despite similar numbers of fibroblasts and hepatocytes across conditions. Phase contrast micrographs of 4 of the 5 configurations (36 $\mu$m, 100 $\mu$m, 480 $\mu$m, and 6800 $\mu$m islands) demonstrated the significant variation in hepatocyte microenvironment which was achieved by altering micropattern dimensions.

Biochemical Analysis Of Liver-Specific Function

To demonstrate the effect of modulation of the local hepatocyte environment on liver-specific function, albumin secretion and urea synthesis were measured as markers of differentiated function. These two markers were measured as a function of micropattern dimensions in the presence and absence of fibroblasts. In cultures of fibroblasts alone, albumin secretion and urea synthesis by fibroblasts was found to be undetectable; therefore, changes in these markers in co-cultures were attributed to differences in hepatocyte metabolism.

Albumin secretion for five different spatial configurations was determined for pure hepatocyte cultures. A rapid decline in liver-specific functions was detected for all five conditions (36 $\mu$m, 100 $\mu$m, 490 $\mu$m, 6800 $\mu$m, and 17,800 $\mu$m islands), from initial values of 8.8±0.9 $\mu$g/day to undetectable levels.

Albumin secretion for the same five micropatterns with the addition of fibroblasts was also measured. Albumin synthesis increased over time in culture in all configurations from less than 10 $\mu$g/day to greater than 34 $\mu$g/day, indicating up-regulation of this liver-specific function due to co-culture with fibroblasts. These micropatterned co-cultures had decreasing amounts of initial heterotypic contact with maximal levels occurring at the smallest hepatocyte island dimension (36 $\mu$m) and minimal levels occurring at the single large hepatocyte island (17.8 mm). Smaller islands with high levels of heterotypic contact demonstrated greater albumin secretion than larger islands (less heterotypic contact) after day 5 of culture. Two fundamental patterns of up-regulation were observed: (1) dramatic up-regulation to similar levels of albumin secretion in the three smallest island configurations (19 to 26-fold of initial levels) and (2) relatively modest up-regulation (~7-fold) in the two larger island configurations. Therefore, a three-fold increase in albumin production was achieved in certain pattern configurations by modulation of the initial cellular microenvironment.

Analysis of urea synthesis in micropatterned co-cultures revealed similar qualitative results. Urea synthesis was either constant over culture or increased from less than ~100 $\mu$g/day to 160 $\mu$g/day indicating up-regulation of another liver-specific function due to co-cultivation with fibroblasts. In addition, two patterns of up-regulation were observed using this marker of differentiated function: (1) up-regulation of urea synthesis to similar levels in the three smallest island configurations (up to 2-fold increase), and (2) relatively little up-regulation in the two larger island configurations. Therefore, a two-fold increase in urea synthesis production was achieved in certain pattern configurations by modulation of the initial cellular microenvironment. Asterisks indicate $p<0.05$ in Tukey post-hoc analysis of variance.

Hepatocyte Function In Situ: Immunostaining Of Intracellular Albumin

In order to further examine the observed variations in liver-specific function exhibited by various micropatterned co-cultures, the hepatocyte phenotype in situ was examined by immunostaining of intracellular albumin. Specifically, these studies first focused on the distribution of albumin staining as it related to the heterotypic interface in one representative pattern, 490 $\mu$m hepatocyte islands (at days 2 and 6). In addition, in order to distinguish between homotypic effects on differentiation and the effects arising from varying the heterotypic interface, immunostaining on micropatterned pure hepatocyte cultures was performed at days 2 and 6. Hepatocytes cultured alone stained uniformly for intracellular albumin at 48 hours after isolation. The level of protein declined subsequently on the order of days. In comparison, micropatterned co-cultures displayed a more complex behavior. They also displayed initial uniform staining for intracellular albumin. Over 6 days, however, hepatocytes close to the heterotypic interface stained for high levels of intracellular albumin, whereas protein levels in hepatocytes far from the heterotypic interface (>3–4 cells) continued to decline as in the pure hepatocyte cultures. To ensure that this 'ring' of intense staining was due to variations in intracellular albumin content of hepatocytes, as opposed to the detachment of hepatocytes or fibroblasts from the lightly-stained areas, phase contrast microscopy of these cultures was performed. The presence of fibroblasts in the periphery of the hepatocyte island and cellular structures in the center of the hepatocyte island was clearly depicted. This peripheral 'ring' of intense staining observed across a 490 $\mu$m micropatterned co-culture was reproducible.

In order to correlate the pattern of immunostaining with the variations that were observed using biochemical analysis of secreted products in media, the distribution of high levels of intracellular albumin in comparatively small (100 $\mu$m) and large (6800 $\mu$m) micropatterned co-cultures was examined. These micrographs demonstrate uniform intense staining in smaller islands (initial island size 100 $\mu$m), a well-demarcated ring of ~120 $\mu$m in intermediate size islands (initial size 490 $\mu$m), and a well-demarcated ring of ~380 $\mu$m in larger islands (initial size 6800 $\mu$m), indicating a negative correlation between differentiated hepatocyte phenotype and distance from the heterotypic interface.

Hepatocyte Function in Situ: Bile Duct Excretion

Another in situ marker of liver-specific function is the formation of functional bile caniliculi between hepatocytes. Carboxyfluorescein diacetate (CFDA) is taken up by hepatocytes, cleaved by intracellular esterases, and in the presence of normal biliary transport, excreted across the apical membrane of the hepatocyte. The presence of normal biliary transport of the dye as well as functional integrity of the tight-junctional domains bounding the caniliculus, causes illumination of visibly fluorescent bile duct structures between hepatocytes. Two patterns were probed: one from a highly functioning co-culture (490 $\mu$m circles) and one from a poorly functioning group (17800 $\mu$m circle), as determined by albumin and urea production, in order to examine this marker of liver-specific function. Phase contrast micrographs of both cultures were produced. The 490 $\mu$m patterns developed functional bile caniliculi, especially in the island periphery, while fluorescent bile duct staining was not observed on 17800 $\mu$m islands.

DISCUSSION

This set of experiments demonstrates that liver-specific tissue function can be modulated by controlling initial heterotypic cell-cell interactions, despite the use of identical cellular components. Furthermore, these differences in bulk tissue properties as a function of cellular microenvironment were generated by induction of spatial heterogeneity in the hepatocyte phenotype. Hepatocytes in the vicinity of the heterotypic interface had a relative increase in levels of liver-specific function; therefore, spatial configurations with maximal initial interface exhibited superior function.

Cellular Microenvironment Modulated Liver-Specific Functions

Evidence that liver-specific function could be controlled by variations in initial cell-cell interactions is seen in the functional differences between predominantly heterotypic co-cultures (smallest islands of 36 $\mu$m diameter) and predominantly homotypic co-cultures (largest island of 17800 $\mu$m diameter) as assessed by markers of metabolism (urea synthesis), synthetic function (albumin secretion and cytoplasmic content), and apical transport (biliary excretion). These cellular microenvironments significantly altered liver-specific functions as follows: increasing hepatocyte island size correlated with a relative decline in urea synthesis, albumin secretion, intracellular albumin staining, and effective biliary excretion. Smaller hepatocyte islands of 36, 100, and 490 $\mu$m initial diameter yielded three-fold steady-state increases in albumin secretion and two-fold steady-state increases in urea synthesis over 6800 and 17800 $\mu$m islands. Similarly, a smaller pattern (490 $\mu$m initial diameter) exhibited functional biliary excretion as assessed by accumulation of a fluorescent compound within bile canilicular structures between hepatocytes whereas larger islands (17,800 $\mu$m initial diameter) showed reduced functional biliary excretion with no evidence of focal fluorescence. The presence of fluorescent biliary structures between hepatocytes has been correlated to biliary structures observed on electron microscopic analysis (LeCluyse et al., 1994, American Physiological Society). The absence of fluorescent biliary structures was attributed to either (1) low rate of excretion across apical domain (2) absence or loss of function of tight junctions at borders of apical membrane or (3) decreased uptake of dye by hepatocytes. The lack of fluorescent biliary structures in 17800 $\mu$m pattern indicates some such functional deficit. Therefore, hepatocytes in smaller island co-cultures have improved biliary transport as well as relative improvements in other liver-specific functions due to alterations in the initial cellular microenvironment (as compared with larger island co-cultures).

In concluding that bulk tissue function (secreted albumin and urea) was modulated by initial cellular microenvironment, hepatocyte numbers were measured to ensure that changes in these liver-specific markers were due to changes in level of hepatocellular function (as opposed to differences in cell division). In order to assess the relative contribution of hepatocyte division, as compared to up-regulation of functions, fibroblasts were growth-arrested, and total DNA in co-cultures was measured. Thus, changes in total DNA could be attributed solely to hepatocytes. Total DNA of co-cultures was measured at 6 hours of co-culture and compared to DNA content at 9 days of co-culture. This analysis demonstrated that no significant increase in total DNA occurred in co-cultures over 9 days, indicating increases in hepatic functions were due to up-regulation of synthesis rather than a marked increase in hepatocyte population (data not shown). These data correlate well with reports of minimal hepatocyte division under various co-culture configurations (Guguen-Guillouzo, 1986, John Libbery Eurotext, INSERM:259–284; Kuri-Harcuch and Mendoza-Figuera, 1989, Differentiation 410:148–157; Donato et al., 1990, In Vitro Cell and Developmental Biology 26:1057–1062). Furthermore, this result correlated well with visual observation of larger micropatterns (490 micron island diameter and greater), where hepatocyte island size was observed to be relatively constant over the course of culture, indicating a lack of significant cell division. Taken together, these data indicate that variations in hepatic functions between culture configurations were due predominantly to relative levels of hepatic upregulation, as opposed to hepatocyte division.

The conclusion that bulk tissue function was modulated by variation of the cell-cell interactions at the heterotypic interface prompted confirmation of similar initial hepatocyte numbers to confirm that changes in secreted products were due to up-regulation of liver-specific functions, rather than differences in numbers of initial hepatocytes. Comparison of initial total hepatocyte DNA in all five micropatterns showed this to be a valid approximation (8±1.8 $\mu$g DNA) with, perhaps, the exception of the smallest (36 $\mu$m) islands which were found to have two-fold elevated levels of DNA. This may be due to the potential for more than one unspread hepatocyte (20 $\mu$m diameter) to adhere to 36 $\mu$m islands. In any event, in these studies, the trend to increased long-term liver specific function resulting from maximal initial heterotypic interface remained a consistent finding.

The experiments described above were conducted with the same surface area dedicated to fibroblasts in all conditions. This allowed examination of the local cellular environment as an isolated variable, without differences in cell numbers and resultant variations in concentrations of potential signaling factors (such as humoral factors in media). In addition, these experiments allowed simultaneous control over both oxygen delivery to hepatocytes, as well as amount of media. In contrast, variation of culture plate area necessitates either a change in media volume to preserve the depth of media above the cell population (and the diffusion of oxygen) or a change in media depth to preserve media volume. Therefore, these methods for controlling cellular environment have definitively demonstrated the importance of local cellular microenvironment as an isolated modulator of liver-specific function (i.e., metabolic and synthetic functions).

Cellular Microenvironment Induced Spatial Heterogeneity in Hepatocyte Phenotype

In addition to demonstrating that liver-specific tissue function can be modulated by controlling initial heterotypic cell-cell interactions, the experiments described herein demonstrate that spatial heterogeneity in the induction of the hepatocyte phenotype was the primary cause of these variations in function. In situ immunostaining of intracellular albumin on micropatterned hepatocyte/fibroblast co-cultures displayed increased staining in the vicinity of the heterotypic interface, indicating up-regulation of this marker of differentiated function. Specifically, smaller (100 $\mu$m islands) stained throughout hepatocyte regions, whereas larger islands (490 $\mu$m and greater) exhibited intense staining in a well-demarcated ring in the periphery. This pattern of staining was highly reproducible both spatially and across various conditions. The differentiated hepatocyte phenotype appeared to dominate within 100–400 $\mu$m of the heterotypic interface; therefore, these data suggest that patterns with greater interfacial regions displayed superior tissue function.

To confirm that variations in intracellular albumin represented variations in hepatocyte phenotype due to heterotypic interactions, the effect of homotypic hepatocyte interactions on the spatial distribution of intracellular albumin in a representative micropattern (490 $\mu$m island) was assessed.

These experiments revealed uniform staining in pure hepatocyte cultures with decreased staining over a period of one week, consistent with the observed decline in secreted albumin and previous studies showing residual albumin mRNA hepatocyte immediately after isolation with decline of mRNA over 1 week; therefore, patterns of immunostaining in co-cultures were indeed due to heterotypic interactions with fibroblasts, rather than homotypic interactions.

Image Analysis:

In order to correlate intracellular albumin staining with albumin secretion data, image analysis was performed on immunostained co-cultures. Specifically, the fraction of hepatocytes contributing to albumin secreted into the media was estimated. Image analysis of intracellular albumin staining revealed ~100% of hepatocytes stained intensely in 100 $\mu$m patterns, ~65% in 490 $\mu$m patterns, and ~20% in 6800 $\mu$m patterns. By assuming a negligible contribution of weakly staining hepatocytes to albumin production, hepatocytes adjacent to the heterotypic interface in larger patterns were estimated to have produced 35–50% more albumin per cell than those in 100 $\mu$m micropatterns. These data suggest there may be a further increase in albumin production in hepatocytes adjacent to relatively undifferentiated homotypic neighbors.

Micropatterning co-cultures, as described above, allowed the creation of larger hepatocyte colonies than those that come about by random aggregation and cell migration; therefore, these assays was able to demonstrate a finite penetration length of a differentiation signal to the interior of a large hepatocyte colony. This result contradicts the notion that hepatocytes are able to communicate effectively throughout a hepatocyte colony.

Related Observations On Control Of Cell-Cell Interactions

While the ability to micropattern co-cultures provides the ability to modulate tissue function via the initial cellular microenvironment, the inherent dynamics of cell adhesion and motility may further modify these engineered tissues in insubstantial ways. The degree of morphogenesis depended upon hepatocyte island size. In these experiments, hepatocyte islands of 490 $\mu$m with center-to-center spacing of 1230 $\mu$m produced a relatively stable configuration whereas hepatocytes in islands of 100 $\mu$m and smaller underwent some reorganization into cord-like structures. Reorganization of tissue may be prevented by cytoskeletal toxins such as cytochalasin D. Despite the tendency for some spatial configurations to reorganize, the perturbations which were achieved in initial cellular microenvironment had significant long-term impact on tissue function.

SUMMARY

These experiments show that micropatterning can be used as a vehicle to control heterotypic cell-cell interactions without significant variations in cell numbers. Indeed, modulation of heterotypic interface as an independent variable was achieved. This modulation of the heterotypic interface over three orders of magnitude dramatically altered levels of detectable liver-specific function in the resulting composite tissues as measured by markers of metabolic, synthetic, and excretory function. Variations in function were due to modulation of the hepatocyte phenotype: specifically, epithelial differentiation varied inversely with distance from the heterotypic interface, causing cultures with a relative increase in cell interaction to exhibit superior function. The ability to control heterotypic cell-cell interactions and probe the resulting tissue for evidence of cell communication has applications both in basic science (e.g., in vitro assays of tissue function) and development of functional tissue constructs for medical applications. From a fundamental perspective, these co-culture techniques can be exploited in assays for determining the mechanisms by which cells communicate. In the area of tissue engineering, the ability to co-cultivate two or more cell types in a micropattern and modulate cell function provides an unprecedented level of control over the in vitro reconstruction of skin, bone marrow, muscle, and many other tissues.

PART III

In the following experiments, microfabrication techniques as well as conventional culture methodologies were used to further examine the mechanism of induction of hepatocyte differentiation at the heterotypic interface. These experiments indicate that the biological signal for the observed induction of hepatic functions is "cell-associated" (broadly defined to include membrane-bound receptors, locally secreted extracellular matrix, and local matrix or cell-bound growth factors), rather than "freely secreted" (broadly defined to include humoral factors such as soluble cytokines and growth factors). Thus, the micropatterning techniques described herein can be used to modulate metabolic and/or synthetic cell functions.

MATERIALS AND METHODS

Examination of the modes of cell communication in hepatocyte/3T3 co-culture was conducted using in situ immunostaining to assess the contribution of homotypic hepatocyte interactions, and various methods of probing the class of signal(s) responsible for induction of the hepatocyte phenotype in hepatocytes proximal to the heterotypic interface. These techniques included pre-treated media to probe for soluble factors (conditioned media), separation of cell populations to probe for labile soluble factors and to eliminate contribution of fibroblast adhering to the hepatocyte surface (spacer), and cultures conducted with continual disturbance of overlying media to probe for transport limitations (agitation).

General Techniques

Methodology for micropatterned substrate preparation, hepatocyte isolation and culture, NIH 3T3-J2 fibroblast culture, immunohistochemistry, analytical assays, and image acquisition are presented in detail above.

Immunostaining Of Micropatterned Cultures

To assess the contribution of hepatocyte homotypic interaction on spatial patterns of albumin immunostaining, various sizes of micropatterned hepatocytes were probed both in the presence and absence of additional fibroblasts. Micropatterned cultures of hepatocytes alone and hepatocyte/fibroblast co-cultures were generated as described above in the following hepatocyte island dimensions: 36, 100, 490, 6800, and 17800 $\mu$m. Hepatocytes were either cultured alone or co-cultured with 750,000 NIH 3T3-J2 fibroblasts. Culture media (2 mL) was replaced daily. Cultures were fixed and stained at 48 hours and 144 hours.

Conditioned Media

Conditioned media experiments were performed in unpatterned configurations. Glass substrates were modified by aminosilane, glutaraldehyde, and collagen I as described in above, resulting in collagen I immobilization over the entire wafer. Hepatocytes were seeded in 'hepatocyte media with serum' as described previously, at a density of 250,000 per P-60. Four different culture configurations were investigated. First, in order to control for baseline degradation of biochemical compounds in media at 37° C., hepatocytes were fed daily with 2 mL of media which had been previously incubated for 24 hours in tissue culture plastic. Second, in order to examine the effects of fibroblast secreted products, hepatocytes were fed daily with 2 mL of media which had previously incubated for 24 hours with (750,000 initially seeded) NIH 3T3-J2 cells on an unmodified glass wafer. Third, in order to probe the effects of fibroblast secreted products which require hepatocyte interaction for their up-regulation, hepatocytes were fed daily with 2 mL of media which had been previously incubated for 24 hours with a co-culture of (750,000 initially seeded) NIH 3T3-J2 cells and 250,000 hepatocytes on an, unpatterned, collagen-modified wafer. Last, in order to generate a 'positive control' to compare the above conditions to co-culture induced up-regulation of liver-specific functions, hepatocytes were co-cultured with NIH 3T3-J2 fibroblasts by the addition of 750,000 NIH 3T3-J2 cells on day 2 of culture. Media was collected daily and stored at 4° C.

Physical Separation Of Cell Types

Figure 3:
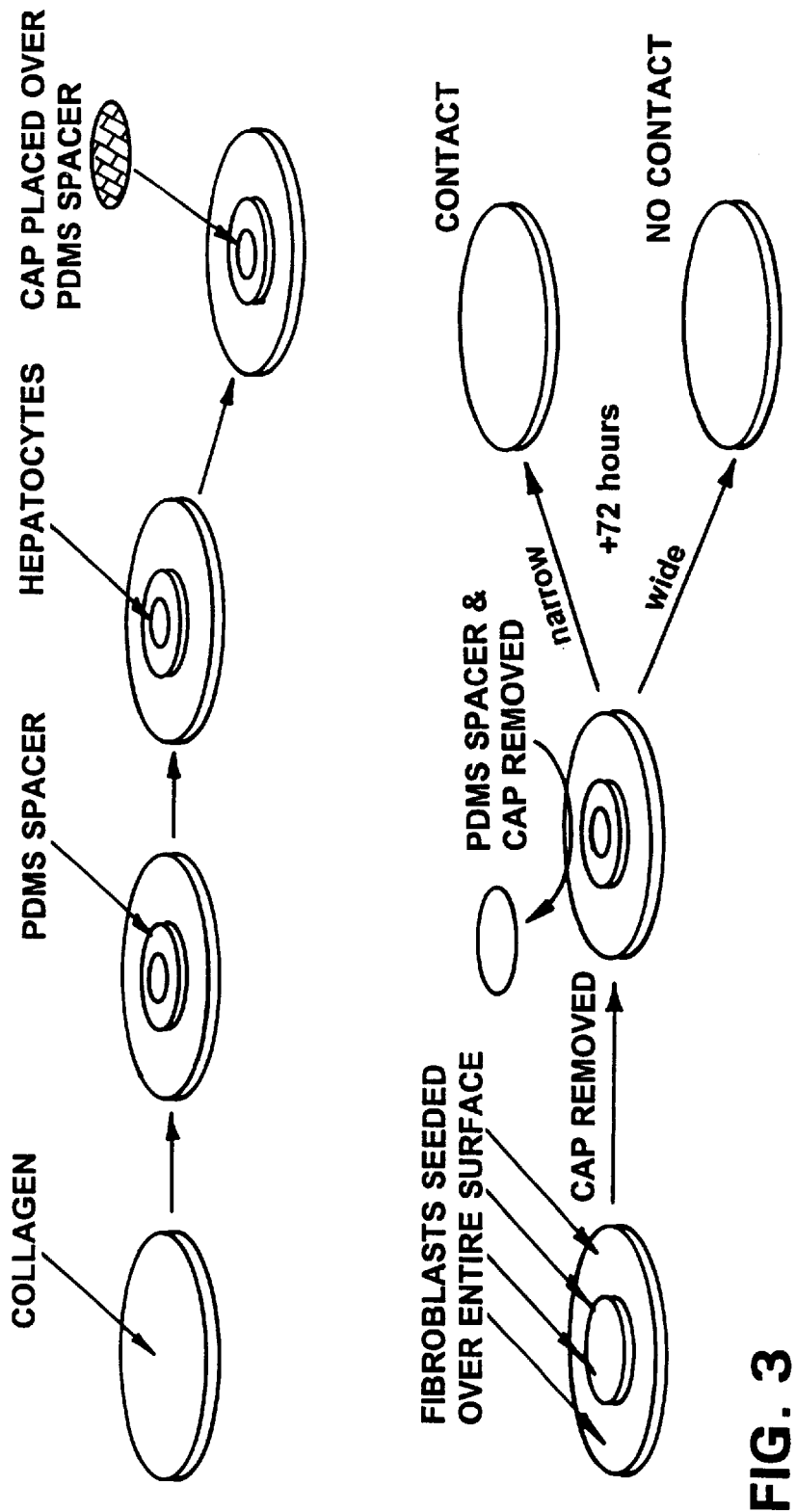
FIG. 3 is a schematic representation of a method to obtain separation of cell populations.

Hepatocytes and fibroblasts were separated by the following general protocol: placement of a polymer annulus on glass substrate, surface modification of glass within the annulus by adsorption of collagen I, attachment of hepatocytes to central, collagen-immobilized region, 'capping' of hepatocyte population during fibroblast seeding to prevent access of fibroblasts to top surface of hepatocytes, and removal of cap and annulus. Differential spacing was achieved by variation in annulus width resulting identical inner diameter (and therefore size of hepatocyte island) and larger outer diameter (resulting in larger separation between cell populations). FIG. 3 depicts a schematic overview of method.

Annuli were fabricated with polydimethysiloxane (PDMS) (Sylgard 184, Dow Corning, Lansing, Mich.). Stock sheets of 500 $\mu$m thickness were prepared by casting polymer solution (mixed as described by the manufacturer) in polystyrene tissue culture plastic for 2 hours at 65° C. Annuli were fabricated with inner diameter of 0.6 cm and various outer diameters using disposable skin punch biopsy cutting tools. To limit potential cytotoxicity, PDMS annuli were then coupled to collagen I with aminoethylaminopropyltrimethoxysilane and glutaraldehyde using conventional methods.

'Caps' were fabricated from sheets of polyethylene teraphthalate (PET) by use of a standard paperpunch to generate 0.6 cm disks from 7 mil thickness mylar film (Kodak). Discs were soaked in 70% ethanol in water for 2 hours followed by rinsing in media.

Annuli were affixed to clean, 2" diameter, borosilicate wafers, and subsequently 'heat-fixed' to prevent detachment via three consecutive exposures to a heat gun at a distance of 10 cm for 5 seconds. Collagen adsorption to the inner circular region of exposed glass was achieved by addition of 200 $\mu$l of collagen I: water in 1:1 ratio, pH 5.0, and incubation at 37° C. for 45 min. Wafers were then sterilized overnight in 70% ethanol in water, rinsed in water, exposed to 0.05% bovine serum albumin and rinsed with serum-free hepatocyte media (as previously described). Hepatocytes were seeded in serum-free media as previously described and allowed to spread overnight.

The following day, PET caps were applied to PDMS annuli under sterile conditions, growth-arrested (mitomycin C treatment described above) fibroblasts were seeded and allowed to attach for 1 hour, rinsed twice with 'fibroblast media', followed by removal of annuli and cap. The separated co-culture was rinsed once more with fibroblast media and fibroblasts were allowed to spread for 6 hours prior to replacement of fibroblast media with 'hepatocyte media with serum'. Control co-culture was performed by methods described previously on 0.68 cm hepatocyte island patterns (as described above). Briefly, glass was modified by immobilization of collagen I, hepatocytes were seeded followed by fibroblasts. No cap or polymer annulus was applied in this condition.

Finally, absence of overlying fibroblasts on hepatocyte island was confirmed using fluorescent labels CMFDA (chloromethylfluorescein diacetate, C-2925, Molecular Probes) and CMFTR (chloromethylbenzoylaminotetramethyl rhodamine, C-2927). Cells were loaded by incubation in 25 $\mu$M dye in media for 45 minutes, rinsed, and incubated for 30 minutes prior to a final rinse. Fibroblasts were then trypsinized as previously described and utilized in the above protocol. Separated co-cultures were rinsed and imaged 7 hours after initial fibroblast seeding.

Agitation

In order to examine the influence of fluid convection on heterogeneity in hepatocyte phenotype, co-cultures were conducted in static and 'shaken' conditions. One representative pattern was utilized for this study. Micropatterned co-cultures were generated utilizing 490 $\mu$m hepatocyte islands with 1230 $\mu$m center-to-center spacing as described previously. 750,000 NIH 3T3-J2 fibroblasts were added 24 hours after initial hepatocyte seeding. Replicate cultures were then cultured under two different conditions: (1) under static culture conditions as previously described and (2) under 'shaken' conditions by culturing on a rocking platform at approximately 1 Hz within a separate incubator. Media (2 mL) was replaced daily. Cultures were fixed and stained for intracellular albumin at indicated times.

RESULTS

Effect Of Homotypic Hepatocyte Interactions On Spatial Pattern Of Immunostaining In these experiments, the potential contribution of homotypic hepatocyte interaction to spatial heterogeneity was examined by studying micropatterns with different levels of homotypic interaction both in the presence and absence of fibroblasts. Patterns of intracellular albumin for five different micropatterned hepatocyte configurations were compared after 48 and 144 hours of culture. Uniform distribution of intracellular albumin was detected at 48 hours in all patterns, which diminished over the time in micropatterned hepatocytes alone. Micropatterned co-cultures (i.e., addition of fibroblasts at 24 hours of culture) displayed a uniform distribution of intracellular albumin similar to that observed in micropatterned hepatocyte cultures. After 6 days of co-culture, however, hepatocytes display differential levels of staining. Hepatocytes far from the heterotypic interface exhibit a similar behavior to hepatocytes cultured in the absence of fibroblasts, low levels of staining. In contrast, hepatocytes proximal to the heterotypic interface exhibit relatively high levels of intracellular albumin. Thus, homotypic hepatocyte interactions do not seem to be the sole contributor to the observed spatial heterogeneity in hepatocyte phenotype.

Use Of Conditioned Media

In order to examine the possible induction of hepatic differentiation by secreted fibroblast products, experiments were conducted with hepatocytes treated with 'conditioned media'. Urea synthesis was measured as a marker of liver-specific function in a variety of such culture conditions. Media was 'conditioned' by 24 hours incubation with (1) tissue culture plastic as a control (hepatocytes+media), (2)

fibroblasts alone (hepatocytes+fibroblast conditioned media), or (3) co-culture of fibroblasts and hepatocytes (hepatocytes of co-culture conditioned media). These data were compared to co-cultured fibroblasts and hepatocytes which served as a positive control for the expected level of liver-specific function (co-culture+media).

These data indicate an expected decline in liver-specific function in pure hepatocyte over the first week of culture to less than 50 µg/day. A similar decline in liver-specific function was observed in cultures treated with fibroblast conditioned media indicating insufficient concentration of humoral factors for induction of hepatic differentiation. In contrast, co-cultures of hepatocyte and fibroblasts displayed up-regulation of urea synthesis from ~60 µg/day to ~175 µg/day over 10 days of culture followed by stable production of urea. Some cultures were treated with co-culture conditioned media to probe for humoral factors present only when both cell types were allowed to communicate. These did not display any further induction of liver-specific function over that observed in co-culture controls, indicating insufficient concentration of humoral factors for induction of hepatic differentiation (detection of urea in this media was due to production of urea by the co-culture utilized for conditioning media—any induction of urea synthesis in the target hepatocyte population would therefore have generated a further increase in urea production over control co-cultures).

Physical Separation Of Cell Populations

Hepatocyte and fibroblast populations were co-cultured in the same dish yet separated by an annulus of bare glass to probe the role of labile, freely secreted factors in induction of hepatic functions. Phase contrast micrographs were produced of two different initial annuli dimensions translating to two different achievable separation widths. Growth-arrested fibroblasts migrated towards the central hepatocyte region at a rate of approximately 500 microns per day. After 3 days, the 1500 µm initial separation was observed to have diminished completely and cell contact occurred at the periphery of the hepatocyte island. Subsequently, cells were allowed to interact for 8 days ('contact' condition). In contrast, initial cell separation of 6000 microns narrowed to 500 microns over the same time frame ('non-contact'). This experimental design allowed the examination of the role of cell proximity/cell contact in induction of hepatic functions as well as the elimination of overlying fibroblasts as confirmed by fluorescent dye labeling.

Hepatocytes in the 'contact' condition exhibited an intense staining pattern in the periphery of the hepatocyte island similar to the peripheral ring of staining observed in the control co-culture. In contrast, hepatocytes in the 'non-contact' condition lacked significant staining for intracellular albumin. These results indicated the importance of cell proximity (<500 µm) for differentiation of hepatocytes. Furthermore, spatial heterogeneity in hepatocyte phenotype persisted despite absence of fibroblast adhesion to surface of hepatocytes, indicating that regional differences in hepatocyte staining is not due to overlying fibroblasts.

Agitation Of Co-Cultures

Another method of examining the potential role of secreted products by fibroblasts was the addition of fluid convection to co-cultures. Under these 'shaken' conditions, humoral factors which theoretically require a high local concentration for their bioactivity would be diluted in the bulk fluid phase and the resulting pattern of hepatocyte differentiation would differ from static conditions. In addition, agitation of culture media would allow mixing of nutrients (oxygen, glucose) and thereby alleviate potential transport limitations to the center of large hepatocyte islands.

The effect of agitation of one representative micropatterned co-culture, 490 µm, as compared to static conditions was measured. Phase contrast micrographs demonstrate that agitation did not cause any overt fibroblast damage due to mechanical shear. In addition, low magnification, bright field images of cultures stained for intracellular albumin demonstrated no significant differences in patterns of spatial heterogeneity. The 'penetration' length of the signal for hepatocyte differentiation from the heterotypic interface did not vary significantly when compared to static cultures. These data suggested (1) spatial heterogeneity of hepatocyte phenotype in static cultures was not caused by significant nutrient limitation due to diffusional transport and (2) dilution of secreted factors by mixing did not modulate the observed pattern of spatial heterogeneity.

DISCUSSION

The experiments summarized above use both conventional and microfabrication techniques to probe in detail the mechanisms by which cells interact. These experiments focused on classification of the signal(s) broadly defined as cell-associated or freely secreted. In addition, these experiments examined potential contributors to the finite 'penetration' length of this signal leading to spatial heterogeneity in the hepatocyte phenotype. The results of these experiments are summarized below.

A Cell-Associated Signal Is Implicated In Induction of Hepatic Function

Experiments to classify the differentiation signal as free versus bound provided evidence that the signal(s) is cell-associated. Taken together, the results of these experiments (use of conditioned media, separation of cell populations within a co-culture, and agitation of micropatterned co-cultures) point towards cell-associated molecules. Neither fibroblast conditioned media nor co-culture conditioned media were able to induce hepatocellular functions in target hepatocytes, indicating the absence of a freely soluble signaling molecule.

The experiments described above indicate that it is implausible that a freely soluble labile signal mediates the induction of hepatic cell function. These data indicated that cell contact (or very close proximity, <5 µm) correlated with induction of liver-specific function in hepatocytes, whereas lack of contact (>500 µm) did not induce an observable signal as measured by immunostaining of intracellular albumin. With the exception of some unique biochemicals such as nitric oxide, other highly labile signals would be expected to signal hepatocytes across 500 µm in this separated culture configuration.

These studies also elucidated the morphology of hepatocytes separated from underlying fibroblasts by a 1 mm thick collagen I hydrogel and observed fibroblastic, de-differentiated morphology after a few days of culture, further suggesting the lack of a freely soluble, highly labile signal (data not shown).

The potential role of freely soluble factors whose bioactivity depends on a high local concentration was also found to be minimal by the combined results of conditioned media and agitation experiments. Any soluble factor which did not induce a signal in conditioned media due to its dilution in the larger media volume, would also be diluted in agitation experiments due to fluid convection in the media. Therefore, if fluid mixing causes reduction of the concentration of some putative soluble signaling factor below its bioactive concentration, one would not expect local induction of hepatocyte function in agitation experiments. In fact, similar patterns of local induction of intracellular albumin were found in hepatocytes in micropatterned co-cultures and static controls, indicating that the dilution of soluble factors was not a critical limitation in induction of hepatocellular function.

Analysis Of The Finite Penetration Length Of Differentiation Signal

With respect to the potential contributors to the spatial heterogeneity observed in the hepatocyte phenotype in co-cultures, the experiments described herein identify three potential contributors thee effects of which can be discounted: (i) inadequate delivery of oxygen or other nutrients to the center of hepatocyte islands, (ii) a primary homotypic effect wherein lack of hepatocyte neighbors in island periphery induced up-regulation of functions, and (iii) heterogeneous signaling from fibroblasts attached to the top surface of hepatocytes.

The role of primary hepatocyte homotypic interactions in induction of spatial heterogeneity of hepatocyte phenotype was not significant. Specifically, when hepatocytes were cultured alone, no spatial variation in intracellular albumin was observed as a result of variations in homotypic interaction. Hepatocytes in small islands exhibited intense, uniform staining similar to staining patterns of hepatocytes both in the periphery and center of larger islands, followed by a spatially uniform decline in liver-specific function at day 6. In contrast, micropatterned co-cultures exhibited marked variations in hepatocyte phenotype where hepatocytes adjacent to the heterotypic interface expressed greater levels of albumin, indicating that spatial heterogeneity is not an artifact of homotypic interactions.

The adequacy of diffusive transport of oxygen and other transport was determined by comparison of static and agitated micropatterned co-cultures. In both cases, a similar pattern of induction was observed at day 4, indicating convective mixing of media did not modify hepatocyte behavior. Finally, the contribution of overlying fibroblasts in the observed spatial heterogeneity was also determined to be minimal. Fibroblasts were noted to adhere to the top surface of spread hepatocytes at larger dimensions of hepatocyte islands with dual label vital dyes and fluorescent microscopy (data not shown); however, experiments performed to separate cell populations effectively prevented fibroblast attachment to the surface of hepatocytes under these conditions. Therefore, the presence of spatial heterogeneity resulting from highly characterized initial conditions was assessed. After 8 days of contact between cell types, intracellular albumin immunostaining indicated the presence of peripheral staining and persistence of the heterogeneous hepatocyte response. Spatial heterogeneity could not be attributed to variations in signals arising from overlying fibroblasts.

Morphogenesis

The role of tissue reorganization on spatial heterogeneity in hepatocyte phenotype was addressed. Notably, reorganization of cultures (both hepatocytes alone and co-cultures) was observed in smaller pattern dimensions and was significantly diminished in large hepatocyte islands (greater than 490 $\mu$m). In these studies, pattern configuration at later time points was perturbed by morphogenesis in the tissue, i.e., observed patterns of staining were determined not only by initial pattern configuration but also by the long-term conformation adopted by the culture. For example, 100 $\mu$m islands did not display spatial heterogeneity in albumin staining, presumably because they reorganized to a pattern where all hepatocytes were proximal to the heterotypic interface. In contrast, 36 $\mu$m islands reorganized to larger dimension 'cord-like' hepatic structures where some hepatocytes were a greater distance from the heterotypic interface, resulting in spatial heterogeneity of hepatocyte phenotype. Despite the existence of some reorganization in these tissues, the fundamental pattern of spatial heterogeneity remained constant; hepatic structures larger than 100 $\mu$m exhibited spatial heterogeneity in hepatocyte phenotype whereas hepatocytes far from the heterotypic interface exhibited low levels of intracellular albumin. Therefore, the conclusions reached above remain well founded.

SUMMARY

In these experiments, conventional culture techniques were combined with microfabricated co-cultures to show that the primary signal for differentiation of hepatocytes in hepatocyte/fibroblast co-cultures is tightly fibroblast-associated. Taken together, the results of conditioned media, separated co-culture, and agitation experiments indicated a 'cell-associated' signal promotes modulation (e.g., up-regulation) of liver-specific functions. The observed finite penetration of the differentiation signal may be due to gap junctional communication, 'tissue phase' diffusion of signaling molecules, and/or physical penetration of fibroblast processes.

With respect to the implications for the design of a co-culture-based bioreactor, evidence that the signal is fibroblast-associated suggests that fibroblasts and hepatocytes should have direct contact (i.e., occupy the same compartment in a bioreactor) to produce adequate levels of liver-specific function. These co-cultures will allow the examination of candidate biochemical signals as well as spatial configurations which minimize the fraction of hepatocytes far from the heterotypic interface, creating the potential for further improvements in bulk tissue function.

Other Embodiments

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for modulating a metabolic or synthetic function of a cell of a first cell type, the method comprising:

i) providing a protein-coated substrate, wherein a protein coating the substrate defines a micropattern on the substrate;

ii) contacting the protein-coated substrate with cells of a first cell type suspended in a first cell medium under conditions such that cells of the first cell type bind the protein of the protein-coated substrate, thereby producing a micropatterned cell-coated substrate; and iii) contacting the micropatterned cell-coated substrate with cells of a second cell type suspended in a second cell medium under conditions such that cells of the second cell type bind the substrate, thereby producing the micropatterned co-culture, wherein:

a) one of the cell media is a selective medium that lacks serum and attachment factors and/or includes a non-adhesive factor to inhibit attachment and one of the cell media is an attachment medium that contains an effective amount of serum and/or at least one attachment factor; and b) the cells of the first and second cell types define a micropattern wherein at least 30% of the cells of the first cell type are within 100 $\mu$m of an interface between the cells of the first cell type and the cells of the second cell type, thereby producing a micropatterned co-culture, wherein a metabolic or synthetic function of a cell of the first cell type is modulated relative to cells of the first cell type in an unpatterned co-culture that comprises cells of the first and second cell types.

2. The method of claim 1, wherein modulation is detected as an increase in protein production of a cell of the first cell type.

3. The method of claim 2, wherein the cells of the first cell type are hepatocytes and modulation is detected as a change in intracellular or secreted albumin of a hepatocyte.

4. The method of claim 2, wherein the cells of the first cell type are hepatocytes and modulation is detected as an change in urea synthesis in a hepatocyte.

5. The method of claim 2, wherein modulation is detected as a change in DNA synthesis in a cell of the first cell type.

6. The method of claim 1, wherein the co-culture comprises a combination of cells selected from the group consisting of:
a) hepatocytes and at least one cell type selected from the group consisting of Kupffer cells, Ito cells, endothelial cells, and biliary ductal cells;
b) endothelial cells and smooth muscle cells;
c) mesenchymal cells and tumorigenic parenchymal cells;
d) bone marrow cells and fibroblasts; and
e) keratinocytes and fibroblasts.

7. The method of claim 1, wherein the co-culture comprises hepatocytes and fibroblasts.

8. A co-culture of cells produced according to the method of claim 1.

9. The method of claim 1, wherein the selective medium is a serum-free medium.

10. The method of claim 1, wherein the attachment medium comprises serum.

11. The method of claim 1, wherein the protein-coated substrate comprises a protein selected from the group consisting of collagen, fibronectin, laminin, and entactin, or combinations thereof.

12. The method of claim 1, wherein the micropattern defined by cells of the first and second cell types comprises an island of cells of the first cell type surrounded by cells of the second cell type.

13. The method of claim 12, wherein the island of cells is 25–1,000 $\mu$m in diameter.

14. The method of claim 13, wherein the island of cells is 30–500 $\mu$m in diameter.

15. The method of claim 14, wherein the island of cells is 100–500 $\mu$m in diameter.

16. The method of claim 1, wherein the rate at which a metabolic or synthetic function is modulated in the micropatterned co-culture is increased relative to the rate at which a metabolic or synthetic function is modulated in an unpatterned co-culture.

17. The method of claim 1, wherein a metabolic or synthetic function of cells of the first cell type is modulated at least 1.5-fold in a micropatterned co-culture, relative to a metabolic or synthetic function of cells of the first cell type in an unpatterned co-culture.

18. The method of claim 17, wherein a metabolic or synthetic function of cells of the first cell type is modulated at least 5-fold in a micropatterned co-culture, relative to a metabolic or synthetic function of cells of the first cell type in an unpatterned co-culture.

19. The method of claim 1, wherein modulation comprises upregulation of a metabolic or synthetic function of a cell.

20. A method for modulating a metabolic or synthetic function of a cell of a second cell type, the method comprising:
i) providing a protein-coated substrate, wherein a protein coating the substrate defines a micropattern on the substrate;
ii) contacting the protein-coated substrate with cells of a first cell type suspended in a first cell medium under conditions such that cells of the first cell type bind the protein of the protein-coated substrate, thereby producing a micropatterned cell-coated substrate; and
iii) contacting the micropatterned cell-coated substrate with cells of a second cell type suspended in a second cell medium under conditions such that cells of the second cell type bind the substrate, thereby producing the micropatterned co-culture, wherein:
a) one of the cell media is a selective medium that lacks serum and attachment factors and/or includes a non-adhesive factor to inhibit attachment, and one of the cell media is an attachment medium that contains an effective amount of serum and/or at least one attachment factor; and
b) the cells of the first and second cell types define a micropattern wherein at least 30% of the cells of the second cell type are within 100 $\mu$m of an interface between the cells of the second cell type and the cells of the first cell type,
thereby producing a micropatterned co-culture, wherein a metabolic or synthetic function of a cell of the second cell type is modulated relative to cells of the second cell type in an unpatterned co-culture that comprises cells of the second and first cell types.

21. The method of claim 20, wherein the co-culture comprises a combination of cells selected from the group consisting of:
a) hepatocytes and at least one cell type selected from the group consisting of Kupffer cells, Ito cells, endothelial cells, and biliary ductal cells;
b) endothelial cells and smooth muscle cells;
c) mesenchymal cells and tumorigenic parenchymal cells;
d) bone marrow cells and fibroblasts;
e) keratinocytes and fibroblasts and
f) hepatocytes and fibroblasts.

22. A co-culture produced according to the method of claim 20.

* * * * *